(12) United States Patent
Cakmak et al.

(10) Patent No.: US 9,587,063 B2
(45) Date of Patent: Mar. 7, 2017

(54) GENERATION OF AMPHIPHILIC NETWORK WITH AN ABILITY TO DISTINGUISH THE TRANSPORT OF IGG AND INSULIN

(71) Applicant: THE UNIVERSITY OF AKRON, Akron, OH (US)

(72) Inventors: Mukerrem Cakmak, Munroe Falls, OH (US); Turgut Nugay, Istanbul (TR); Nihan Nugay, Istanbul (TR); Joseph Kennedy, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/896,074

(22) PCT Filed: Jun. 5, 2014

(86) PCT No.: PCT/US2014/041100
§ 371 (c)(1),
(2) Date: Dec. 4, 2015

(87) PCT Pub. No.: WO2014/197699
PCT Pub. Date: Dec. 11, 2014

(65) Prior Publication Data
US 2016/0122458 A1    May 5, 2016

Related U.S. Application Data

(60) Provisional application No. 61/831,233, filed on Jun. 5, 2013.

(51) Int. Cl.
| | | |
|---|---|---|
| *C08F 290/06* | (2006.01) | |
| *C08G 77/442* | (2006.01) | |
| *A61L 27/16* | (2006.01) | |
| *C08F 230/08* | (2006.01) | |
| *C08G 77/38* | (2006.01) | |

(52) U.S. Cl.
CPC .......... *C08F 290/068* (2013.01); *A61L 27/16* (2013.01); *C08F 230/08* (2013.01); *C08G 77/38* (2013.01); *C08G 77/442* (2013.01)

(58) Field of Classification Search
CPC ..................................................... C08G 77/20
USPC .......................................... 526/279; 528/32
See application file for complete search history.

(56) References Cited

U.S. PATENT DOCUMENTS

| | | | |
|---|---|---|---|
| 3,450,736 A | | 6/1969 | Monterrey |
| 5,049,617 A | * | 9/1991 | Yoshioka .............. C08F 291/00 525/104 |
| 2003/0022991 A1 | | 1/2003 | Kennedy et al. |
| 2007/0238176 A1 | | 10/2007 | MacDonald et al. |
| 2010/0048818 A1 | | 2/2010 | Kennedy et al. |
| 2010/0209468 A1 | | 8/2010 | Kennedy et al. |

FOREIGN PATENT DOCUMENTS

WO    WO 2008/019044    *  2/2008

OTHER PUBLICATIONS

"High Strength Bimodal Amphiphilic Conetworks for Immunoisolation Membranes: Synthesis, Characterization, and Properties" authored by Guzman et al. and published in Macromolecules (2015) 48, 6251-6262.*

"Polyvinylpyrrolidone-polydimethylsiloxane Amphiphilic Co-networks: Synthesis, Characterization, and Perm-selective Behavior" authored by Zhang et al. and published in the Journal of Applied Polymer Science (2016) 133, 42985.*

* cited by examiner

*Primary Examiner* — Marc Zimmer
(74) *Attorney, Agent, or Firm* — Renner Kenner Greive Bobak Taylor & Weber

(57) ABSTRACT

A method of preparing an amiphiphilic co-network comprising preparing a molecularly-bimodal crosslinkable amphiphilic graft by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture where the molar mass ratio between average molar mass of the first asymmetric-telechelic monomer mixture polydihydrocarbylsiloxane and average molar mass of the second asymmetric-telechelic monomer mixture polydihydrocarbylsiloxane is between 1:2 and 1:20; and crosslinking the molecularly-bimodal crosslinkable amphiphilic graft with a siloxane compound that includes at least two Si—H bonds.

18 Claims, 21 Drawing Sheets

- Compression mold medical grade TPU pallets to get two circular, flat films
- Compression mold the circular parts in scaffold mold
- Precise holes added into parts using 23G needle holding parts attached together on a clamp
- BAP membrane material is drop cast on the

GENERATION OF AMPHIPHILIC NETWORK WITH AN ABILITY TO DISTINGUISH THE TRANSPORT OF IGG AND INSULIN

CROSS-REFERENCE TO RELATED APPLICATIONS

This application claims priority from U.S. Provisional Patent Application No. 61/831,223 filed on Jun. 5, 2013, the contents of which are incorporated herein by reference.

FIELD OF THE INVENTION

One or more embodiments relates to amiphiphilic co-networks preparable by crosslinking a molecularly-bimodal crosslinkable amphiphilic graft.

BACKGROUND OF THE INVENTION

Amphiphilic networks have been found useful as membranes for providing immunoisolatory features in bioartifical organs. Amphiphilic polymer networks can serve as a means to encapsulate and thereby immunoisolate implantable biologically active moieties. Films made from amphiphilic polymer networks have also been found to be desirable in the production of contact lenses. It has been found that current amphiphilic networks crack when dried due to development of stresses during drying.

Presently a need in the art exists for an amphiphilic co-network with improved mechanical properties that is resistant to cracking. There is also a need in the art for an amiphiphilic co-network that can selectively exclude or allow the diffusion of certain molecular species.

SUMMARY OF THE INVENTION

A first embodiment provides a method of preparing an amiphiphilic co-network comprising preparing a molecularly-bimodal crosslinkable amphiphilic graft by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture where the molar mass ratio between average molar mass of the first asymmetric-telechelic monomer mixture polydihydrocarbylsiloxane and average molar mass of the second asymmetric-telechelic monomer mixture polydihydrocarbylsiloxane is between 1:2 and 1:20; and crosslinking the molecularly-bimodal crosslinkable amphiphilic graft with a siloxane compound that includes at least two Si—H bonds.

A second embodiment provides a method as in the first embodiment, where the second asymmetric-telechelic polydihydrocarbylsiloxane monomer mixture is 0.1% to 10% of the total asymmetric-telechelic polydihydrocarbylsiloxane monomer.

A third embodiment provides a method as in the either the first or second embodiment, where the first asymmetric-telechelic polydihydrocarbylsiloxane monomer mixture includes:

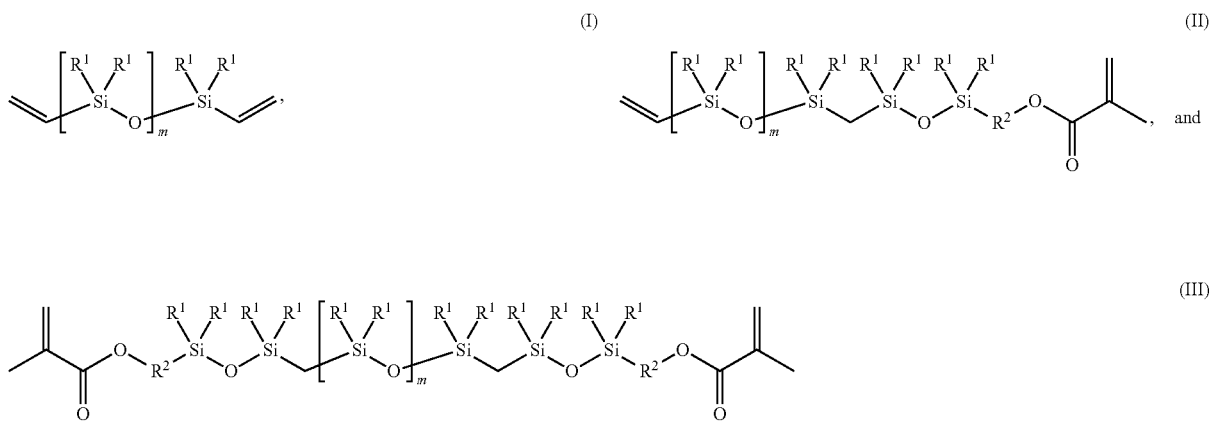

where each $R^1$ is individually a monovalent organic group, each $R^2$ is individually a divalent organic group, and each m is individually an integer from about 190 to about 320 units.

A forth embodiment provides a method as in any of the first through third embodiments, where the first asymmetric-telechelic polydihydrocarbylsiloxane monomer mixture is prepared by reacting a vinyl telechelic polydihydrocarbylsiloxane with a disiloxane acrylate with a telechelic polydihydrocarbylsiloxane to disiloxane acrylate molar ratio of less than 1:2; where the vinyl telechelic polydihydrocarbylsiloxane is defined by the formula

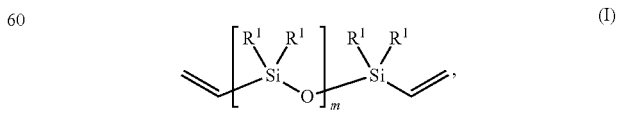

where each $R^1$ is individually a monovalent organic group, and wherein the disiloxane acrylate defined by the formula

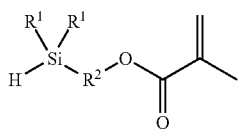

(IV)

where each $R^1$ is individually a monovalent organic group, and $R^2$ is a divalent organic group.

A fifth embodiment provides a method as in any of the first through forth embodiments, where each $R^1$ is an alkyl group of 1 to 6 carbon atoms.

A sixth embodiment provides a method as in any of the first through fifth embodiments, where the second asymmetric-telechelic polydihydrocarbylsiloxane monomer mixture includes the following:

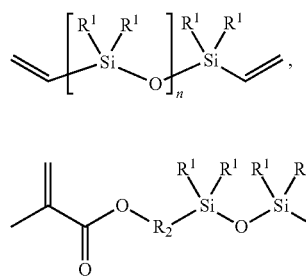

(V)

(VI)

(VII)

where each $R^1$ is individually a monovalent organic group, each $R^2$ is individually a divalent organic group, and each n is individually an integer from about 1100 to about 1900.

A seventh embodiment provides a method as in any of the first through sixth embodiments, where the second asymmetric-telechelic polydihydrocarbylsiloxane monomer mixture is prepared by reacting a vinyl telechelic polydihydrocarbylsiloxane with a disiloxane acrylate with a telechelic polydihydrocarbylsiloxane to disiloxane acrylate molar ratio of less than 1:2; where the vinyl telechelic polydihydrocarbylsiloxane is defined by the formula (VIII)

where each $R^1$ is individually a monovalent organic group, and each n is individually an integer from about 1100 to about 1900; and wherein the disiloxane acrylate defined by the formula (IV)

where each $R^1$ is individually a monovalent organic group, and $R^2$ is a divalent organic group.

An eighth embodiment provides a method as in any of the first through seventh embodiments, where each $R^1$ is an alkyl group of 1 to 6 carbon atoms.

A ninth embodiment provides a method as in any of the first through eighth embodiments, where the dihydrocarbylacrylamide monomer is defined by the formula (IX)

where each $R^3$ is individually a monovalent organic group.

A tenth embodiment provides a method as in any of the first through ninth embodiments, where the dihydrocarbylacrylamide monomer is defined by the formula

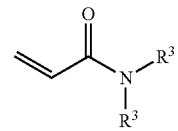

(X)

An eleventh embodiment provides a method as in any of the first through tenth embodiments, where the dihydrocarbylacrylamide monomer is between 40 and 60 wt % of the total weight of the dihydrocarbylacrylamide monomer, first asymmetric-telechelic polydihydrocarbylsiloxane monomer mixture, and second asymmetric-telechelic polydihydrocarbylsiloxane monomer mixture.

A twelfth embodiment provides a method as in any of the first through eleventh embodiments, where the step of crosslinking the molecularly-bimodal crosslinkable amphiphilic graft with a siloxane compound that includes at least two Si—H bonds includes the use of a Karstedt catalyst to facilitate crosslinking.

A thirteenth embodiment provides a method as in any of the first through twelfth embodiments, where the siloxane compound that includes at least two Si—H bonds is defined by the formula

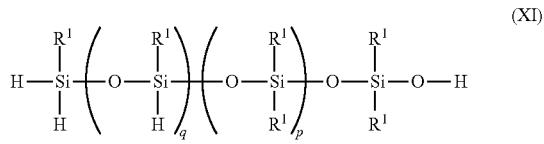

(XI)

where each $R^1$ is individually a monovalent organic group, q is an integer from about 1 to about 2000 and p is an integer from about 1 to about 2000.

A fourteenth embodiment provides a method as in any of the first through thirteenth embodiments, where each $R^1$ is an alkyl group of 1 to 6 carbon atoms.

A fifteenth embodiment provides an amiphiphilic co-network prepared by any of the first through fourteenth embodiments.

A sixteenth embodiment provides a bio-artificial organ comprising a housing with a plurality of holes on the housing, over the plurality of holes, an amiphiphilic co-network prepared by any of the first through fourteenth embodiments.

A seventeenth embodiment provides a bio-artificial organ as in the sixteenth embodiment, where the housing comprises a first disc with a with a first raised ring around the perimeter of the disc and a concentric smaller second raised ring within the first raised ring, and a second disc with a raised ring, the raised ring of the second disc situated between the first and second raised rings of the first disc, wherein a void is present between the first disc, the second raised ring of the first disc, and the second disc, and the first disc, the second disc or both discs include a plurality of holes that connect to said void.

An eighteenth embodiment provides a bio-artificial organ as in any of the sixteenth through seventeenth embodiments, where the first raised ring and second raised ring of the first disc includes a cut out portion, and the raised ring of the second disc includes a cutout portion aligned with the cut out portion of the first disc.

DETAILED DESCRIPTION OF ILLUSTRATIVE EMBODIMENTS

Figure 1:
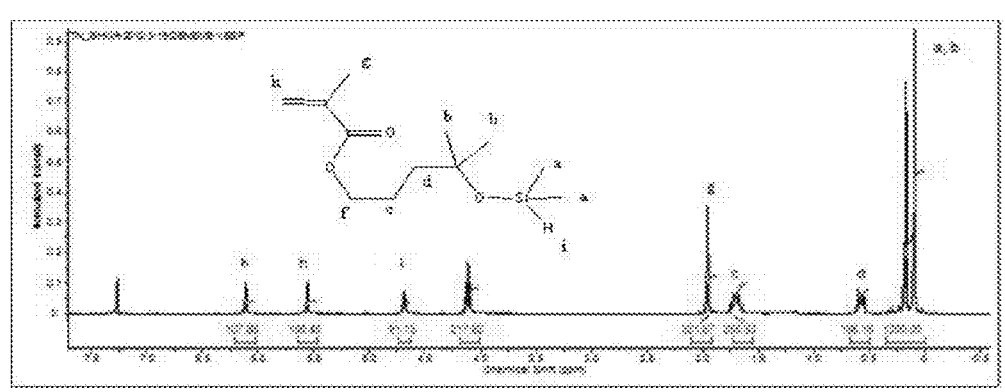
FIG. 1 provides a chart of the $^1$H NMR spectrum of 2-propionic acid 3-(1,1,3,3-tetramethyldisiloxaniyl)propyl-ester (SiH-MA)

One or more embodiments provides a method of preparing an amiphiphilic co-network comprising preparing a molecularly-bimodal crosslinkable amphiphilic graft by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture where the molar mass ratio between average molar mass of the first asymmetric-telechelic monomer mixture polydihydrocarbylsiloxane and average molar mass of the second asymmetric-telechelic monomer mixture polydihydrocarbylsiloxane is between 1:2 and 1:20; and crosslinking the molecularly-bimodal crosslinkable amphiphilic graft with a siloxane compound that includes at least two Si—H bonds. Advantageously it has been found that when a second, higher molecular weight asymmetric-telechelic polydihydrocarbylsiloxane monomer mixture is used in conjunction with a first asymmetric-telechelic polydihydrocarbylsiloxane monomer mixture, the resultant amiphiphilic co-network exhibits better mechanic properties and resists to cracking when dried.

The amphiphilic co-network is a polymer network that includes a hydrophobic constituent and a hydrophilic constituent. The hydrophobic constituent and the hydrophilic constituent are interconnected to create a cocontinuous morphology of hydrophobic phases and hydrophilic phases, which allows the amphiphilic co-network to have both hydrophobic pores and hydrophilic pores. The cocontinuous morphology allows the amphiphilic co-network to bipercoluate, or, in other words, allow solvents of different polarity, such as water and a hydrocarbon, to permeate separately from edge to edge of the entire amphiphilic co-network. In one or more embodiments, substantially all of the hydrophobic constituents and hydrophilic constituents are crosslinked. Substantially all of the hydrophobic constituents and hydrophilic constituents are crosslinked when there is no appreciable loss of permeability in the amphiphilic co-network. The amphiphilic co-network may be a hydrogel that swells in both water and hydrocarbons.

The molecularly-bimodal crosslinkable amphiphilic graft includes a hydrophobic constituent and a hydrophilic constituent. The hydrophilic constituent forms a backbone carrying hydrophobic branches. Each branch may include a crosslinkable end group. The molecularly-bimodal crosslinkable amphiphilic graft may include first set of hydrophobic branches and a second set of hydrophobic branches, were the second set of hydrophobic branches has a longer chain length. In one or more embodiments, the molecularly-bimodal crosslinkable amphiphilic graft may be soluble (e.g. in THF). The molecularly-bimodal crosslinkable amphiphilic graft may be crosslinked to from an amiphiphilic co-network.

As noted above, the molecularly-bimodal crosslinkable amphiphilic graft is prepared by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture. An asymmetric-telechelic polydihydrocarbylsiloxane monomer mixture refers to a mixture of polydihydrocarbylsiloxane monomers that include two different terminal functional groups that allow for further reaction or polymerization. The asymmetric-telechelic polydihydrocarbylsiloxane monomer mixture may include a polydihydrocarbylsiloxane monomer (PDHS), with two first terminal functional groups (A) in a telechelic monomer (A-PDHS-A), a polydihydrocarbylsiloxane monomer, with two second terminal functional groups (B) in a telechelic monomer (B-PDHS-B), and a polydihydrocarbylsiloxane monomer, with first terminal functional groups and a second terminal functional groups in a di-end-functional monomer (A-PDHS-B).

In one or more embodiments, the molar mass ratio between average molar mass of the monomers in the first asymmetric-telechelic monomer mixture polydihydrocarbylsiloxane and average molar mass of the monomers in the second asymmetric-telechelic monomer mixture polydihydrocarbylsiloxane is between about 1:2 and about 1:20, in other embodiments between about 1:8 and about 1:15, in other embodiments between about 1:4 and about 1:10, and in other embodiments between about 1:5 and about 1:8.

In one or more embodiments, the second asymmetric-telechelic polydihydrocarbylsiloxane monomer mixture is 0.1% to 10%, in other embodiments 0.5% to 7%, and in other embodiments 1% to 5% of the total asymmetric-telechelic polydihydrocarbylsiloxane monomer. The total polydihydrocarbylsiloxane monomer is the sum of all of the polydihydrocarbylsiloxane monomer mixtures.

In one or more embodiments, the first asymmetric-telechelic polydihydrocarbylsiloxane monomer mixture includes:

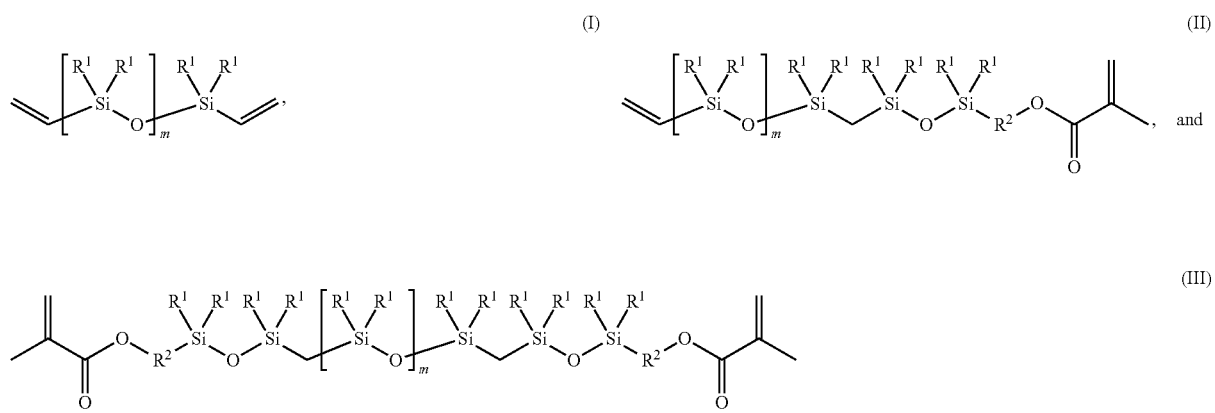

where each $R^1$ is individually a monovalent organic group, each $R^2$ is individually a divalent organic group. In one or more embodiments, the each m group of the first asymmetric-telechelic polydihydrocarbylsiloxane monomer mixture is individually an integer from about 100 to about 500, in other embodiments from about 180 to about 350, in other embodiments from about 190 to about 320, in other embodiments from about 195 to about 315.

In one or more embodiments, the monovalent organic $R^1$ groups of the first asymmetric-telechelic polydihydrocarbylsiloxane monomer mixture are each individually alkyl groups of 1 to 6 carbon atoms. In one or more embodiments, the monovalent organic $R^1$ groups of the first asymmetric-telechelic polydihydrocarbylsiloxane monomer mixture are methyl groups. In one or more embodiments, the divalent organic $R^2$ groups of the first asymmetric-telechelic polydihydrocarbylsiloxane monomer mixture are each individually divalent alkane groups of 1 to 6 carbon atoms.

In one or more embodiments, the first asymmetric-telechelic polydihydrocarbylsiloxane monomer mixture includes:

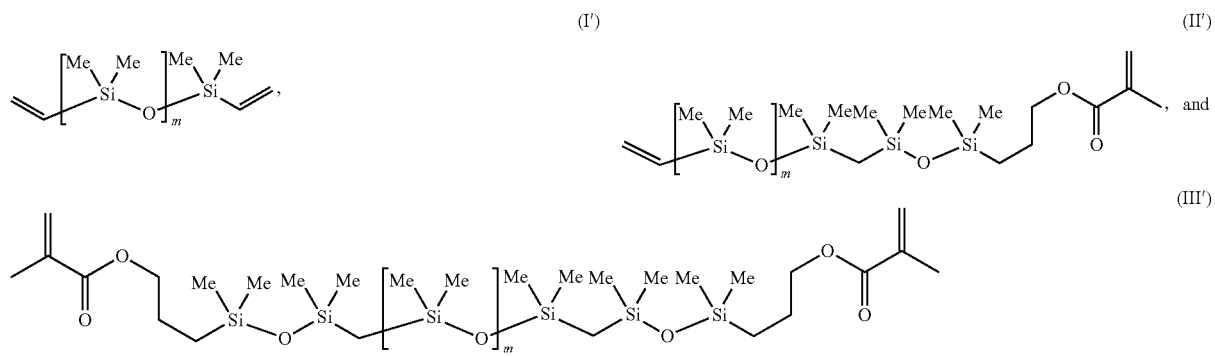

where m is defined as above.

In one or more embodiments, the second asymmetric-telechelic polydihydrocarbylsiloxane monomer mixture includes the following:

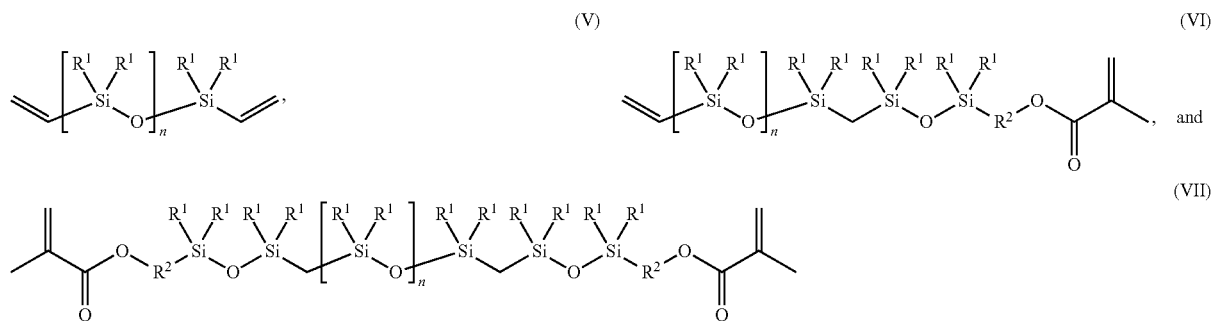

where each $R^1$ is individually a monovalent organic group, each $R^2$ is individually a divalent organic group. In one or more embodiments, the each n group of the second asymmetric-telechelic polydihydrocarbylsiloxane monomer mixture is individually an integer from about 1000 to about 2000, in other embodiments from about 1050 to about 1950, in other embodiments from about 1100 to about 1900, in other embodiments from about 1150 to about 1850.

In one or more embodiments, the monovalent organic $R^1$ groups of the second asymmetric-telechelic polydihydrocarbylsiloxane monomer mixture are each individually alkyl groups of 1 to 6 carbon atoms. In one or more embodiments, the monovalent organic $R^1$ groups of the second asymmetric-telechelic polydihydrocarbylsiloxane monomer mixture are methyl groups. In one or more embodiments, the divalent organic $R^2$ groups of the second asymmetric-telechelic polydihydrocarbylsiloxane monomer mixture are each individually divalent alkane groups of 1 to 6 carbon atoms.

In one or more embodiments, the second asymmetric-telechelic polydihydrocarbylsiloxane monomer mixture includes the following:

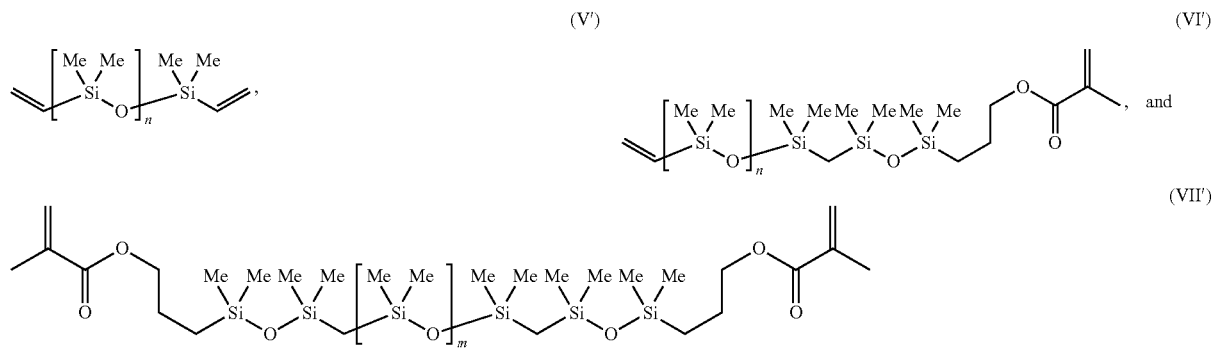

where n is defined as above.

The first asymmetric-telechelic polydihydrocarbylsiloxane monomer mixture and the second asymmetric-telechelic polydihydrocarbylsiloxane monomer mixture may be prepared together or separately. In one or more embodiments, the asymmetric-telechelic polydihydrocarbylsiloxane monomer mixture is prepared by reacting a vinyl telechelic polydihydrocarbylsiloxane with a disiloxane acrylate. A telechelic polydihydrocarbylsiloxane to disiloxane acrylate molar ratio of less than 1:2 is used to produce an asymmetric-telechelic polydihydrocarbylsiloxane monomer mixture that includes asymmetric-telechelic polydihydrocarbylsiloxane monomer vinyl and acrylate end groups. In one or more embodiments, the telechelic polydihydrocarbylsiloxane to disiloxane acrylate molar ratio less than 1:2, in other embodiments less than 1:1.5, in other embodiments less than 1:1. In one or more embodiments, where the first asymmetric-telechelic polydihydrocarbylsiloxane monomer mixture and the second asymmetric-telechelic polydihydrocarbylsiloxane monomer mixture are prepared together, a first vinyl telechelic polydihydrocarbylsiloxanes and a second vinyl telechelic polydihydrocarbylsiloxane with a longer chain length are reacted with a disiloxane acrylate in the same reaction mixture.

The reaction between a telechelic polydihydrocarbylsiloxane and the disiloxane acrylate is a hydrosylation reaction. In one or more embodiments a platinum catalyst may be used to facilitate the hydrosylation telechelic polydihydrocarbylsiloxane and the disiloxane acrylate. Suitable platinum catalysts include Karstedt's catalysts.

In one or more embodiments, the disiloxane acrylate suitable for use in preparing the first or the second asymmetric-telechelic polydihydrocarbylsiloxane monomer mixture defined by the formula

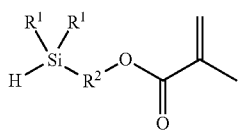

(IV)

where each $R^1$ is individually a monovalent organic group, and $R^2$ is a divalent organic group.

In one or more embodiments, the vinyl telechelic polydihydrocarbylsiloxane suitable for use in preparing a first asymmetric-telechelic polydihydrocarbylsiloxane monomer mixture is defined by the formula

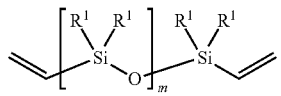

(I)

where each $R^1$ is individually a monovalent organic group. In one or more embodiments, the m group of the vinyl telechelic polydihydrocarbylsiloxane is an integer from about 100 to about 500, in other embodiments from about 180 to about 350, in other embodiments from about 190 to about 320, in other embodiments from about 195 to about 315.

In one or more embodiments, the vinyl telechelic polydihydrocarbylsiloxane suitable for use in preparing a first asymmetric-telechelic polydihydrocarbylsiloxane monomer mixture is defined by the formula

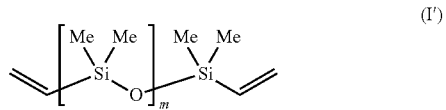

(I')

where m is defined as above.

In one or more embodiments, the vinyl telechelic polydihydrocarbylsiloxane suitable for use in preparing a second asymmetric-telechelic polydihydrocarbylsiloxane monomer mixture is defined by the formula

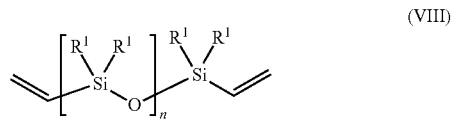

(VIII)

where each $R^1$ is individually a monovalent organic group. In one or more embodiments, the n group of the vinyl telechelic polydihydrocarbylsiloxane is an integer from about 1050 to about 1950, in other embodiments from about 1100 to about 1900, in other embodiments from about 1150 to about 1850.

In one or more embodiments, the vinyl telechelic polydihydrocarbylsiloxane suitable for use in preparing a first asymmetric-telechelic polydihydrocarbylsiloxane monomer mixture is defined by the formula

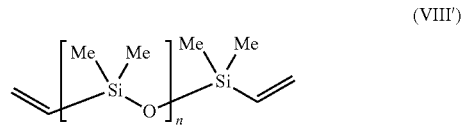

(VIII')

where n is defined as above.

The first asymmetric-telechelic polydihydrocarbylsiloxane monomer mixture and the second asymmetric-telechelic polydihydrocarbylsiloxane monomer mixture may be combined with a dihydrocarbylacrylamide monomer. The dihydrocarbylacrylamide monomer may polymerized to prepare the molecularly-bimodal crosslinkable amphiphilic graft. The polymerization may take place under free radical conditions. In one or more embodiments the dihydrocarbylacrylamide monomer may be between about 40 and about 70 wt %, in other embodiments about 45 and about 65 wt %, and in other embodiments about 50 and about 60 wt % of the total weight of the dihydrocarbylacrylamide monomer, first asymmetric-telechelic polydihydrocarbylsiloxane monomer mixture, and second asymmetric-telechelic polydihydrocarbylsiloxane monomer mixture.

In one or more embodiments, the dihydrocarbylacrylamide monomer may be defined by the formula

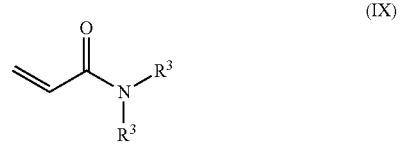

(IX)

where each R³ is individually a monovalent organic group. In one or more embodiments, where the monovalent groups are each methyl groups, the dihydrocarbylacrylamide monomer may be defined by the formula

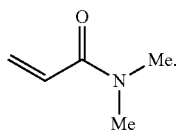
(IX')

As noted above, molecularly-bimodal crosslinkable amphiphilic graft is crosslinked with a siloxane compound that includes at least two Si—H bonds. The crosslinking reaction between the crosslinkable amphiphilic graft and the siloxane compound that includes at least two Si—H bonds is a hydrosylation reaction. In one or more embodiments a platinum catalyst may be used to facilitate the hydrosylation telechelic polydihydrocarbylsiloxane and the disiloxane acrylate. Suitable platinum catalysts include Karstedt's catalysts.

In one or more embodiments, the amount of siloxane compound that includes at least two Si—H bonds may be characterized in reference to the amount of vinyl end groups present in the molecularly-bimodal crosslinkable amphiphilic graft. In one or more embodiments, the vinyl group to Si—H bond ratio is about 1:1 to about 1:30, in other embodiments about 1:3 to about 1:25, and in other embodiments about 1:5 to about 1:10.

In one or more embodiments, the amount of siloxane compound that includes at least two Si—H bonds may be characterized by the percent weight of the siloxane compound that includes at least two Si—H bonds of the total of the molecularly-bimodal crosslinkable amphiphilic graft and the siloxane compound that includes at least two Si—H bonds. In one or more embodiments, the weight percent of the siloxane compound that includes at least two Si—H bonds is from about 1% to about 30%, in other embodiments from about 3 to about 25%, and in other embodiments about 5% to about 10%. Suitable siloxane compounds that includes at least two Si—H bonds for crosslinking the crosslinkable amphiphilic graft may be found in U.S. Pat. Nos. 8,247,515 and 8,067,521, both of which are incorporated by reference. In one or more embodiments, the siloxane compound that includes at least two Si—H bonds may be defined by the formula

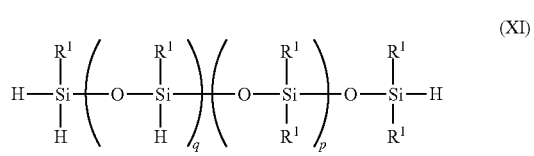
(XI)

where each R¹ is individually a monovalent organic group. In one or more embodiments, q is an integer from about 1 to about 2000, in other embodiments, from 3 to 100, in other embodiments, 5 to 50, and in other embodiments, 10 to 30. p is an integer from about 1 to about 2000. In one or more embodiments, p is an integer from about 1 to about 2000, in other embodiments, from 3 to 100, in other embodiments, 5 to 50, and in other embodiments, 10 to 30.

In one or more embodiments, the siloxane compound that includes at least two Si—H bonds may be defined by the formula

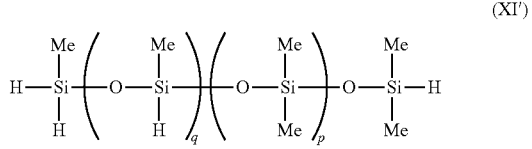
(XI')

where p and q are defined as above.

Monovalent organic groups suitable for use in amphiphilic co-network include linear branched or cyclic substituted or unsubstituted alkyl and aryl groups that include from 1 to 6 carbon atoms, in other embodiments from 2 to 4 carbon atom and in other embodiments, 3 carbon atoms. Suitable substitutions include replacing a hydrogen or a carbon atom with an oxygen atom, nitrogen atom, sulfur atom, or a halogen atom. In one or more embodiments, the monovalent organic group is an alkyl of 1 to 6 carbon atoms. Suitable alkyl group of 1 to 6 carbon atoms include, but are not limited to, methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, sec-hexyl, and cyclohexyl groups.

Divalent organic groups suitable for use in amphiphilic co-network include linear branched or cyclic substituted or unsubstituted alkane and aromatic group that include from 1 to 6 carbon atoms, in other embodiments from 2 to 4 carbon atom and in other embodiments, 3 carbon atoms with two hydrogen atoms removed to create two valances. Suitable substitutions include replacing a hydrogen or a carbon atom with an oxygen atom, nitrogen atom, sulfur atom, or a halogen atom. In one or more embodiments, the divalent organic group may be an alkane of 1 to 6 carbon atoms two hydrogen atoms removed. Suitable alkane of 1 to 6 carbon atoms include groups for use as divalent groups include, but are not limited to, methane, ethane, propane, isopropane, isobutane, tertbutane, n-butane, sec-butane, isopentane, tertpentane, n-pentane, sec-pentane, terthexane, n-hexane, isohexane, sec-hexane, and cyclohexane groups.

Advantageously, the amphiphilic co-network may be prepared with controlled pore diameters. The pore diameter of the amphiphilic co-network is the width of the opening of pore. In one or more embodiments, the amphiphilic co-network may be used as a membrane in a bio-artificial organ. In order to avoid hyperacute rejection, the antibodies of the bio-artificial organ recipients of should be prevented from "seeing" the foreign proteins and activating complement. The amphiphilic co-network should also reliably safeguard the patient from infectious processes (e.g., bacteria) unwittingly transferred with the bio-artificial organ. The pore diameters of the amphiphilic co-network used for immunoisolation may be of a sufficient size to allow insulin, glucose, oxygen, and carbon dioxide to pass freely. These molecules have diameters less than 35 Angstroms (3.5 nm). The pore diameters of the amphiphilic co-network used for immunoisolation may also be of a sufficient size exclude the immigration of immunoglobulins, complement, and cytokines (e.g., tumor necrosis factor) providing immunoisolation. In one or more embodiments, the amphiphilic co-network has hydrophilic pore dimensions in the range of about 3.0 nm to about 4.0 nm.

In one or more embodiments, the bio-artificial organ may be a bio-artificial pancreas. Advantageously, it has been found that the amphiphilic co-network allows the rapid diffusion of insulin, but is impermeable to immunoglobulin G (IgG). Suitable bio-artificial pancreas are disclosed in U.S. Pat. Nos. 8,247,515; 8,067,521; 8,702,810 and all of which are incorporated by reference.

In one or more embodiments, the bio-artificial organ comprises a housing with a plurality of holes on the housing, over the plurality of holes, an amphiphilic co-network. In these or other embodiments, the housing of the bioartifical organ, which may be referred to as a scaffold, comprises a first disc with a with a first raised ring around the perimeter of the disc and a concentric smaller second raised ring within the first raised ring, and a second disc with a raised ring, the raised ring of the second disc situated between the first and second raised rings of the first disc, wherein a void is present between the first disc, the second raised ring of the first disc, and the second disc, and the first disc, the second disc or both discs include a plurality of holes that connect to said void. The first raised ring and second raised ring of the first disc may include a cut out portion, and the raised ring of the second disc may include a cutout portion aligned with the cut out portion of the first disc. The cut out portion may be adapted to fill the void. In one or more embodiments the void is filled with islets of langerhorn.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Synthesis of Poly(N,N-dimethylacrylamide)/Polydimethylsiloxane Conetworks a) Synthesis of 2-propionic acid 3-(1,1,3,3-tetramethyldisiloxanyl)propyl ester (SiHMA)

The synthesis strategy for SiHMA is given by the following scheme:

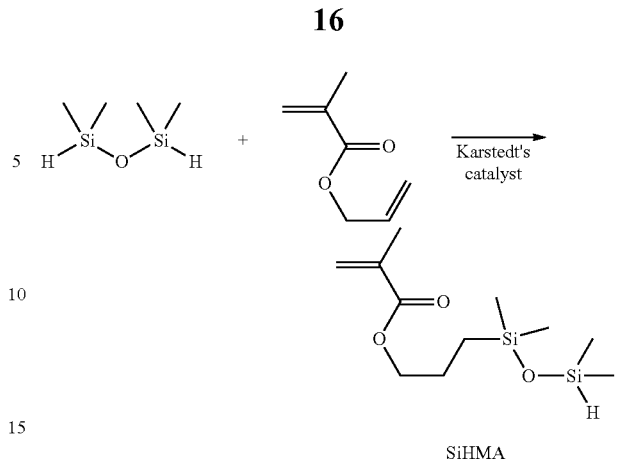

SiHMA

Thus, tetramethyldisiloxane (134 g, 1 mol) and allyl methacrylate (126 g, 1 mol) were placed in a round bottom flask. The reaction was started by the addition of Karstedt's catalyst (0.5 mL) and the mixture was stirred for 3 h. Then triphenylphosphine (10 mL) was added and the charge was vacuum distilled at 50° C. The product (SiHMA) is a colorless liquid with a boiling point of 62° C. Proton NMR spectroscopy confirmed tyhe expected structure (FIG. 1).

The spectrum shows a multiplet at 4.67 ppm, which indicates the presence of the SiH group, and the characteristic resonances at 6.2 and 5.6 ppm (for the olefinic protons) and at 1.9 ppm (for the methyl protons) are associated with the methacrylate (MA) group.

b) Synthesis of the Asymmetric-Telechelic Macromonomer (MA-PDMS-V)

Molecularly-bimodal crosslinkable branches (MA-PDMS-V) of bAPG were prepared by combining SiHMA with two different molecular weight (17,200 and 117,500 g/mol) vinyl ditelechelic PDMSs (V-PDMS-V)s by hydrosilation.

The following scheme shows the transformations and the structure of the products:

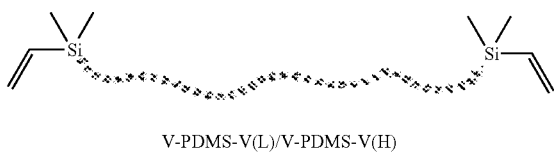

V-PDMS-V(L)/V-PDMS-V(H)

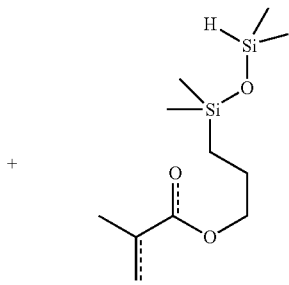

SiHMA

Karstedts's catalyst

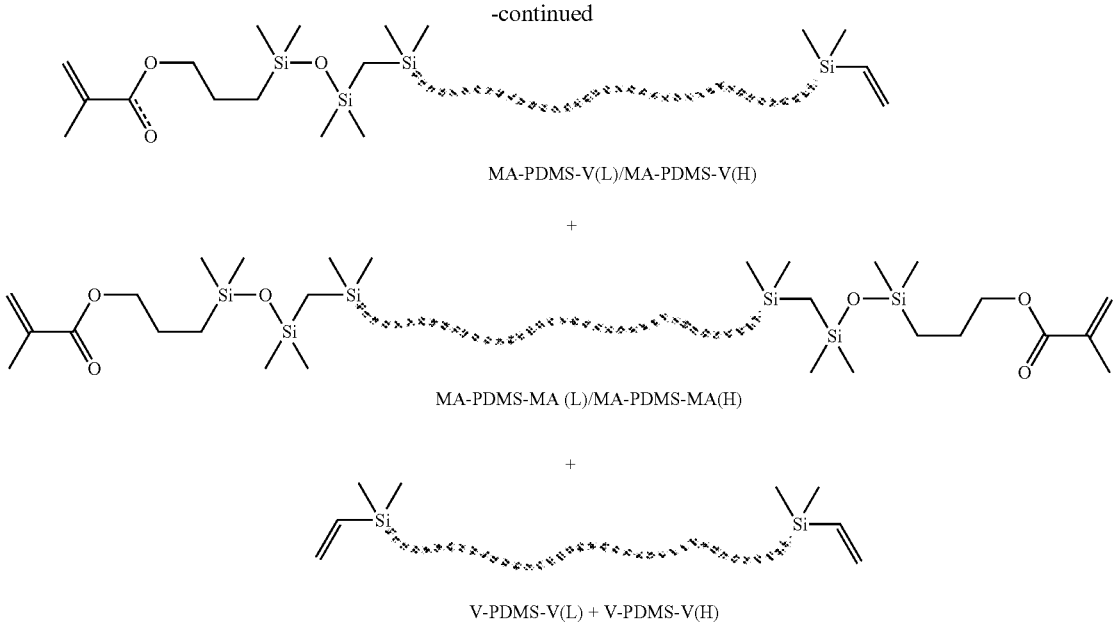

MA-PDMS-V(L)/MA-PDMS-V(H)

+

MA-PDMS-MA (L)/MA-PDMS-MA(H)

+

V-PDMS-V(L) + V-PDMS-V(H)

In this scheme the dotted line stands for the low or high molecular weight PDMSs.

Thus, V-PDMS-V and SiHMA were placed in a 500 mL round bottom flask and dissolved in freshly distilled toluene at room temperature. Then various compositions (1-5%) high molecular weight V-PDMS-V(H) and low molecular weight V-PDMS-V(L) were added to the system. Reagent quantities and stoichiometry are shown in Table 1. Hydrosilation was started by the addition of Karstedt's catalysts, and the charge was stirred while heating at 50° C. for 2 h.

neously integrated into the graft. The shift of the elution peaks toward increased molecular weights with increasing amount of MA-PDMS-V further indicates the incorporation of the high molecular weight MA-PDMS-V.

c) Synthesis of [PDMAAm(PDMS)]-g-PDMS-V (bAPG)

The free radical terpolymerization of DMAAm plus MA-PDMS-V and MA-PDMS-MA yields a bAPG consisting a

TABLE 1

Reaction Conditions for the Preparation of Assymeric Telechelic MA-PDMS-V Macromer*

|  | MA-PDMS-V-0 | MA-PDMS-V-1 | MA-PDMS-V-2 | MA-PDMS-V-5 |
|---|---|---|---|---|
| V-PDMS-V(L) (17200 g/mol) | 0.250 mmol (100%) | 0.248 mmol (99%) | 0.245 mmol (98%) | 0.238 mmol (95%) |
| V-PDMS-V(H) (117500 g/mol) | — | $2.5 \times 10^{-3}$ mmol (1%) | $5.0 \times 10^{-3}$ mmol (2%) | $12.5 \times 10^{-3}$ mmol (5%) |

*Each compositions contained SiHMA = 0.25 mmol, Karstedt catalyst (3% xylene solution) = 0.02 mL, and toluene = 23 mL.

Figure 2:
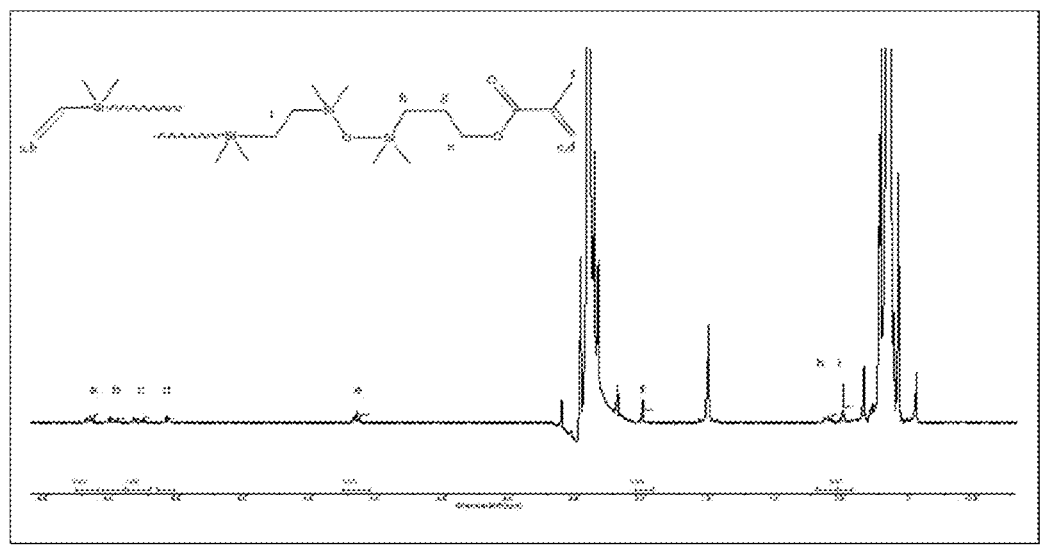
FIG. 2 provides a chart of the $^1$H NMR Spectrum of MA-PDMS-V.
Figure 3:
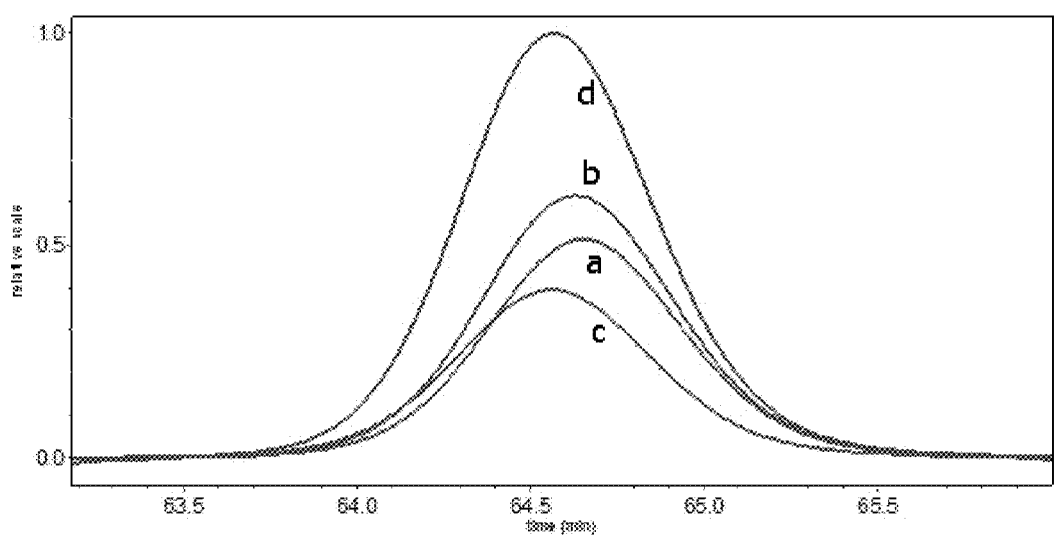
FIG. 3 provides a chart of the GPC traces of a) MA-PDMS-V-0, b) MA-PDMS-V-1, c) MA-PDMS-V-2 and d) MA-PDMS-V-5.

The product was characterized by $^1$H NMR spectroscopy and GPC. (FIGS. 2 and 3)

The resonances associated with the SiH proton (4.67 ppm) disappeared. The resonance for the $CH_2$ protons, which arose by hydrosilation of $—Si—CH=CH_2$ by SiHMA, appears at 0.4 ppm.

According to the symmetrical monomodal GPC traces, the high molecular weight MA-PDMS-V was homoge- PDMAAm backbone carrying -PDMS-V branches. The vinylsilyl termini do not copolymerize with the MA groups under free radical conditions; therefore the bAPG remains soluble. The following scheme helps to visualize the synthetic strategy:

Mixture of MA-PDMS-V(L)/MA-PDMS-V (H), MA-PDMS-MA(L)/MA-PDMS-MA (H) and V-PDMS-V(L)/V-PDMS-V (H) (see scheme in b) above)

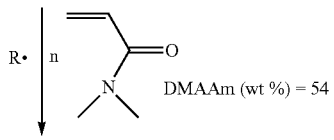

DMAAm (wt %) = 54

-continued

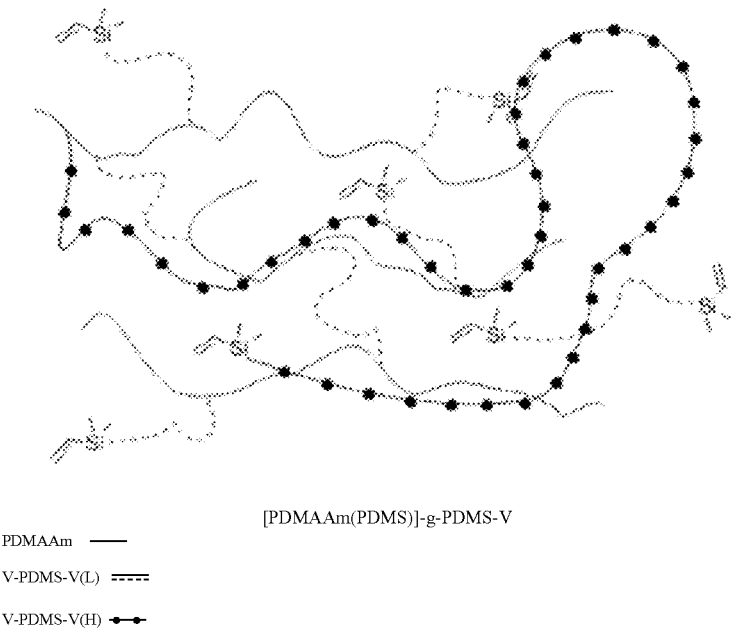

[PDMAAm(PDMS)]-g-PDMS-V

PDMAAm ——

V-PDMS-V(L) - - - - -

V-PDMS-V(H) •—•

Thus, freshly distilled DMAAm (3.57 g), various mixtures of 0, 1, 2 and 5% low and high molecular weight MA-PDMS-V (total=0.25 mmol), and 65 mL toluene were placed in a 500 mL round bottom flask and stirred under a nitrogen atmosphere. Then AIBN (5.36 mg) was added and the solution was stirred at 65° C. for 24 h. The solvent was evaporated under vacuum and the solid bAPG was recovered. Conversion was found to be quantitative.

Depending on the overall composition, i.e., on the amount of low and high molecular weight MA-PDSM-V, the products were optically clear rigid (MA-PDMS-V-0 and MA-PDMS-V-1) or flexible (MA-PDMS-V-2 and MA-PDMS-V-5) materials.

Figure 4:
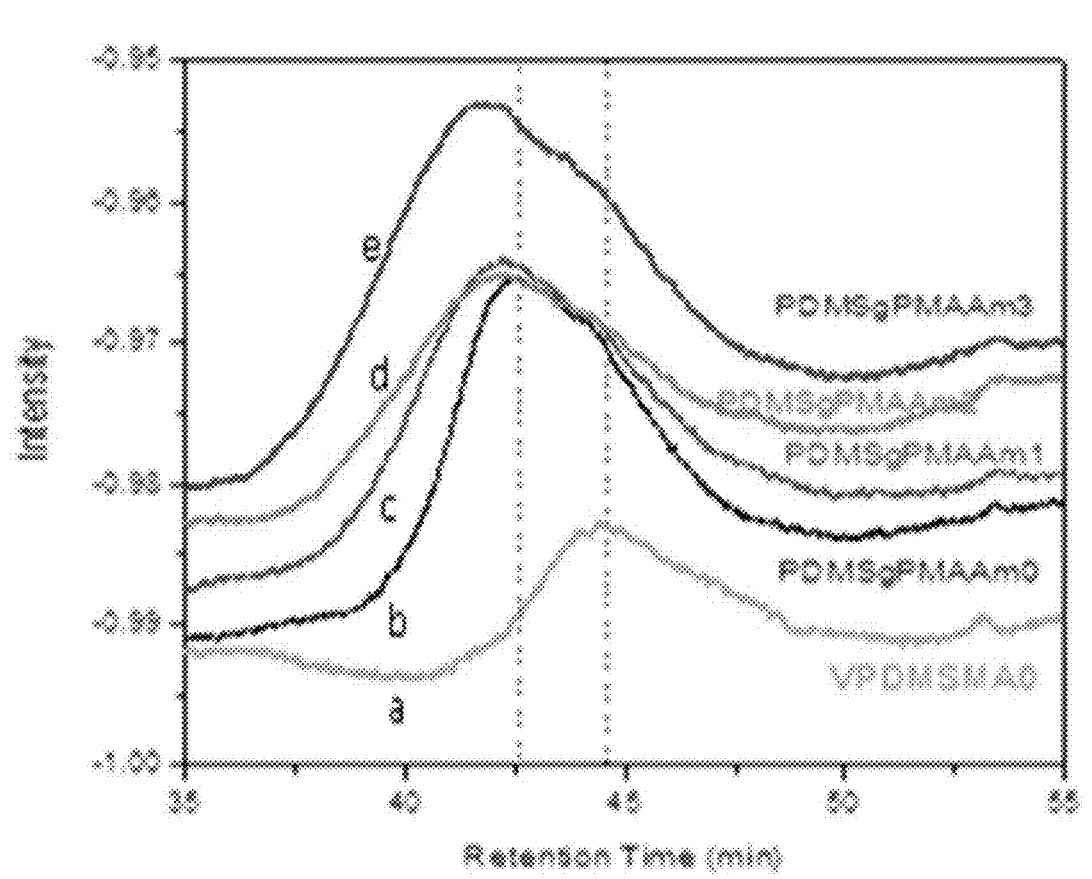
FIG. 4 provides a chart of GPC traces of a) V-PDMS-MA, b) [PDMAAm(PDMS)]-g-PDMS-V-0, c) [PDMAAm(PDMS)]-g-PDMS-V-1, d) [PDMAAm(PDMS)]-g-PDMS-V-2, e) [PDMAAm(PDMS)]-g-PDMS-V-5.

FIG. 4 shows GPC traces of the four representative grafts containing 0, 1, 2, and 5% V-PDMS-MA(H), and the V-PDMS-MA for comparison.

The position of the main elution peak of V-PDMS-MA shifts to lower retention times (higher molecular weights) with increasing V-PDMS-MA concentration, which indicates successful grafting. Moreover, the noticeable broadening of the peaks with increasing V-PDMS-MA(H) content suggests that the presence of V-PDMS-MA(H) did not affect grafting efficiency or architectural homogeneity.

d) Crosslinking the bAPG to bAPCN and the Preparation of Membranes

The molecularly-bimodal amphiphilic graft was crosslinked by hydrosilation of the pendant -PDMS-V branches by the use of a polyhydrosiloxane-PDMS copolymer (PHMS-co-PDMS). The structure of the crosslinker was:

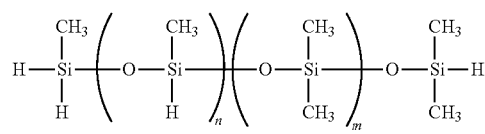

Crosslinker: PHMS-co-PDMS: 30 mol % PHMS

The following equation shows the network formation effected by the use of this crosslinker, and the structure of the target bAPCN membrane: [PDMAAm(PDMS)]-g-PDMS-V

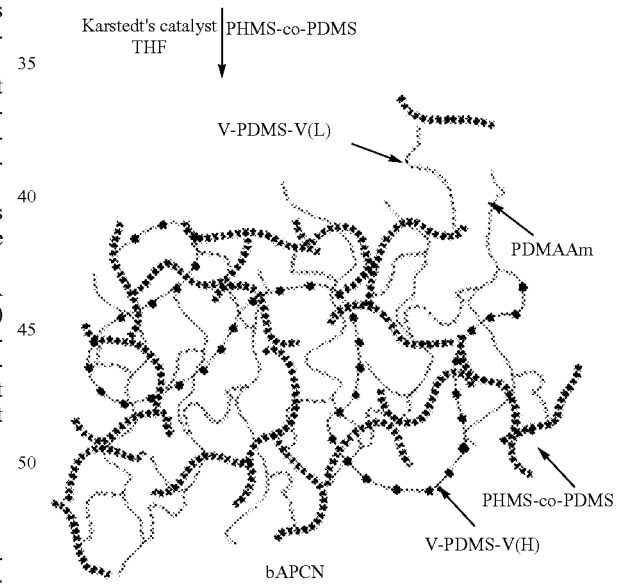

A series of four membranes were prepared as follows:
Four bAPGs ([PDMAAm(PDMS)]-g-PDMS-V of 0, 1, 2, and 5%) (0.9 g) were mixed with the above crosslinker in three ratios (allyl chain end/hydrosiloxane molar ratio=1:5, 1:10 and 1:25), and crosslinked with a Karstedt's catalyst (25 μL) in THF (8 mL) solvent. The bAPGs were homogenized with the crosslinker in THF common solvent by strong stirring for 10 min under a nitrogen atmosphere. Then the homogeneous solution was poured on a Teflon sheet and thin films of controlled thicknesses were prepared using a doctor's blade. The film then was kept at room temperature overnight and subsequently cured at 70° C. for 24 h. All the bAPCN films were homogeneous and optically clear.

Curing Properties

Figure 5:
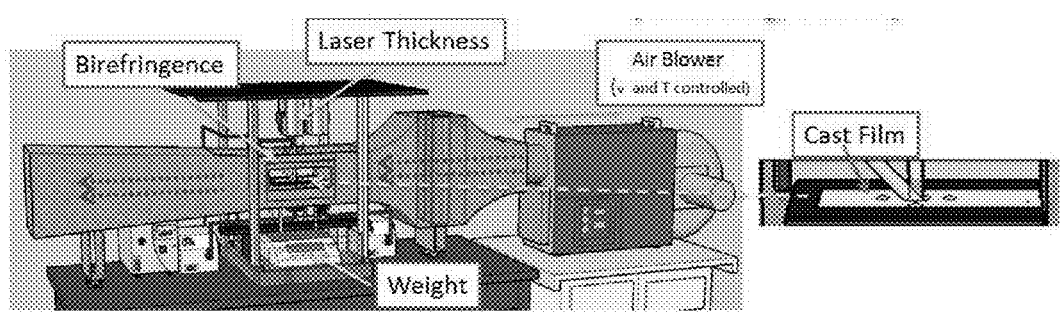
FIG. 5 provides a schematic of an instrumented system that tracks weight, thickness and birefringence and surface temperature of cast coatings during their solidification (JOEY).

Instrumented device (internally called JOEY) developed to track the thickness, weight, birefringence of coating during drying (patent pending) was used to track temporal changes in these physical parameters during the curing of the membrane. This real-time instrument (FIG. 5) follows in-plane and out-of-plane birefringence, weight, thickness, and surface temperature during the course of solvent evaporation and crosslinking of membrane. The membrane is cast on a glass substrate with thickness controlled Dr. Blade with an initial casting gap of 400 μm then placed into JOEY for testing.

Figure 6:
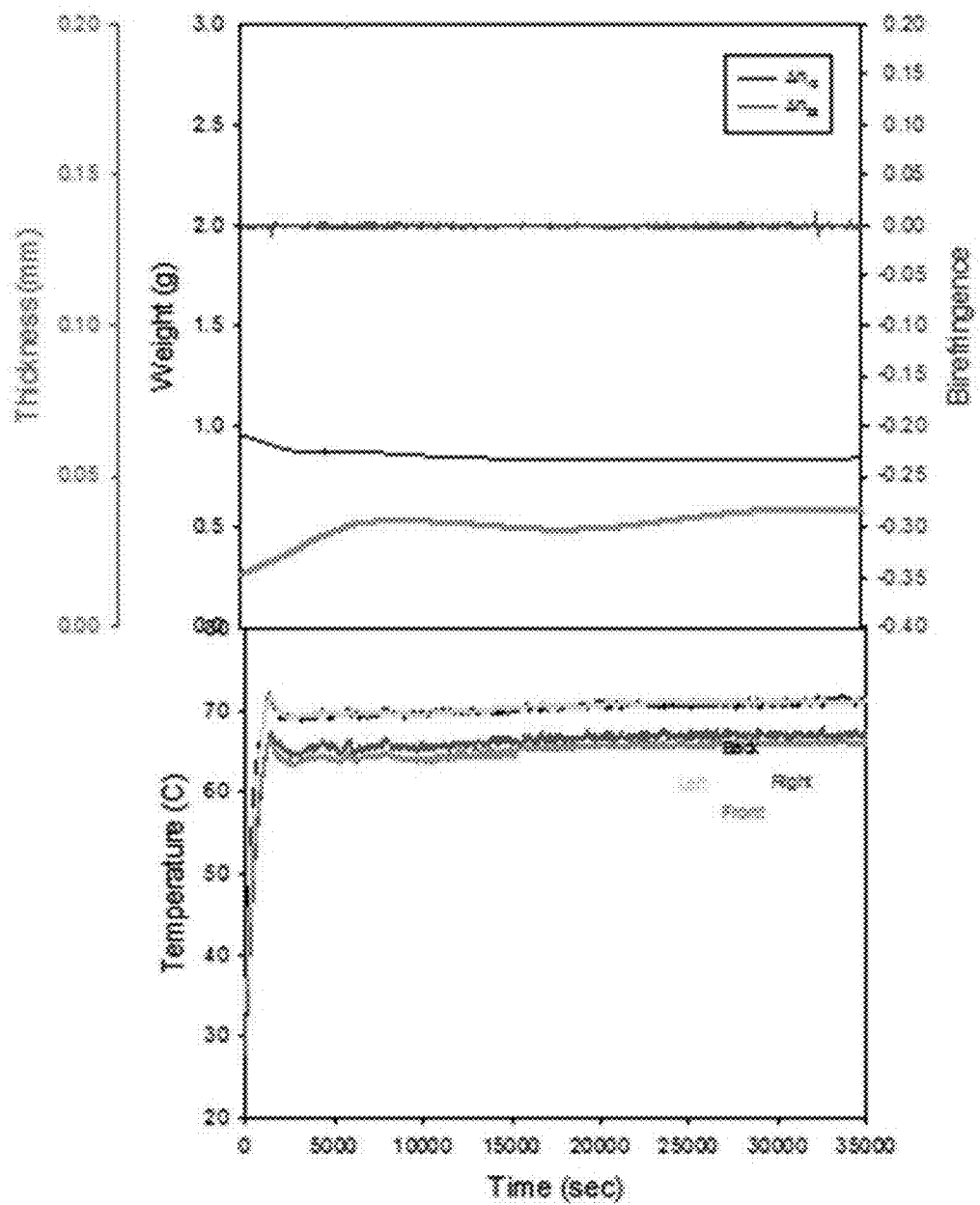
FIG. 6 is a graph showing curing properties of 1% PDMS APCN membrane with 1:25 crosslinking ratio.

As shown in FIG. 6. Weight rapidly decreased in first 5000 seconds as solvent evaporates at early stages. Following this initial stage, the rate of weight reduction decreased substantially and continue to decrease until the end of curing. No changes in birefringence is observed during drying and crosslinking. The thickness increase during curing may be related to undulations created during the process.

Mechanical Properties

The mechanical and mechano-optical properties of the APCN membrane were measured using a unique computer controlled machine that was developed at The University of Akron, in the Polymer Engineering Department. This machine is equipped with two opposing crossheads that move in synch with each other and the strain on the sample is measured by laser micrometer that measures the width at the symmetry midplane as well as high speed video that records the locations of four painted dots on the dumbbell shaped sample. Birefringnece is continuously monitored by spectral birefringnece system developed in Cakmak's research group. The details of the stretching-birefringence apparatus were reported earlier. Dumbbell samples of 40.5 (gauge length=19.5 mm) by 25 mm were stretched at room temperature at a stretching rate of 100 mm/min.

Mechanical Properties

Figure 7:
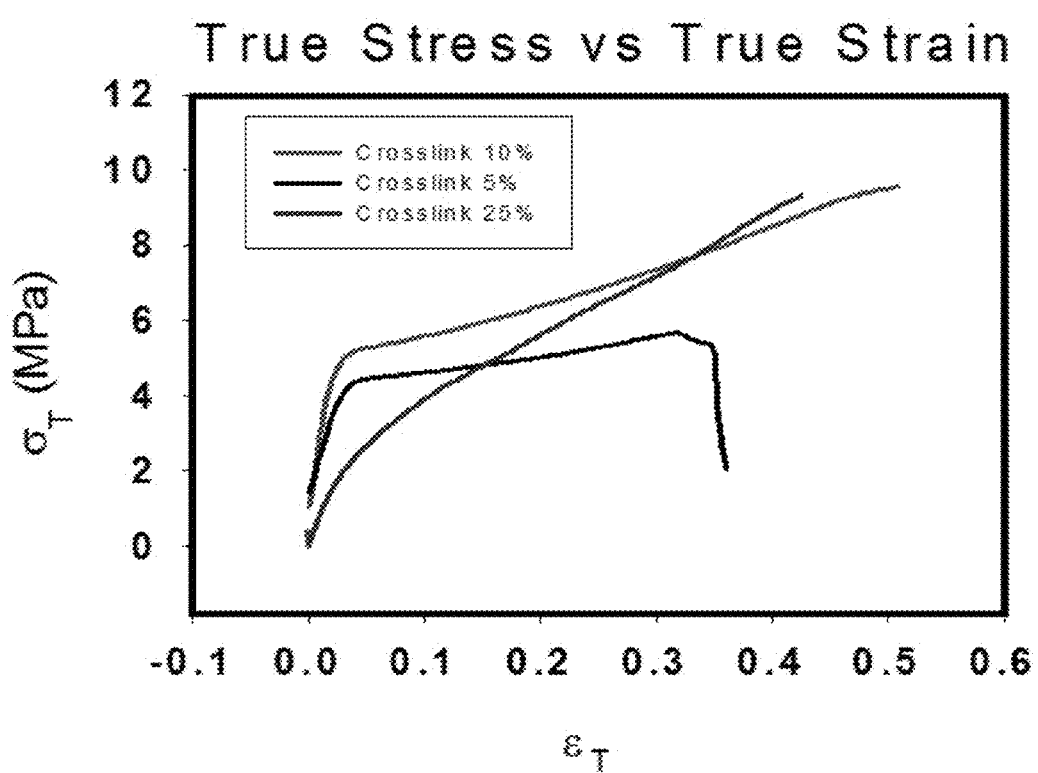
FIG. 7 is a graph showing mechanical property comparisons between 2% PDMS APCN membranes with different crosslinking ratios.
Figure 8:
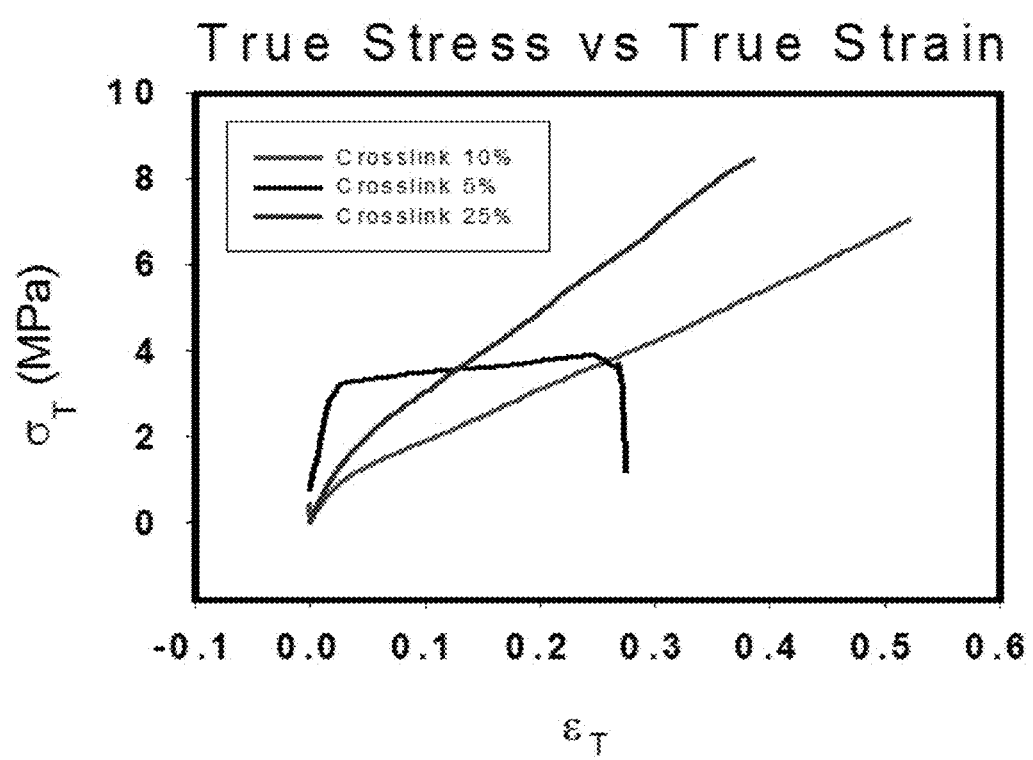
FIG. 8 is a graph showing mechanical property comparisons between 5% PDMS APCN membranes with different crosslinking ratios.

FIGS. 7 and 8 shows the mechanical properties of 2% PDMS APCN and 5% films with three different crosslink levels 5, 10, 25%. Over 5% crosslink the elongation to break and tensile strength increases in these films indicating superior mechanical properties are obtained in these membranes that is suited for production of membranes and with these mechanical properties their survival after implantation is greatly enhanced.

The polymers with a higher concentration of both the HMW PDMS and crosslinker exhibited the best mechanical properties.

Figure 9A:
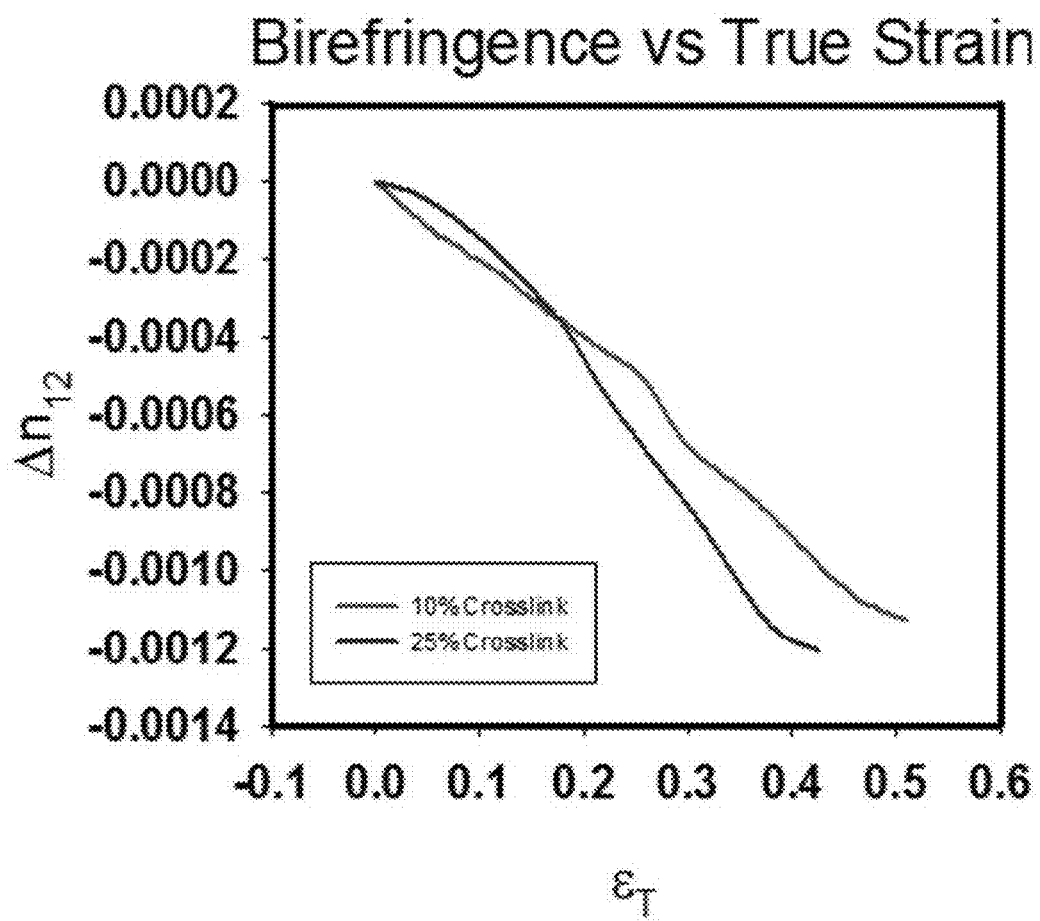
FIG. 9A is a graph showing mechanicano-optical property comparisons between 2% PDMS APCN membranes with different crosslinking ratios.
Figure 9B:
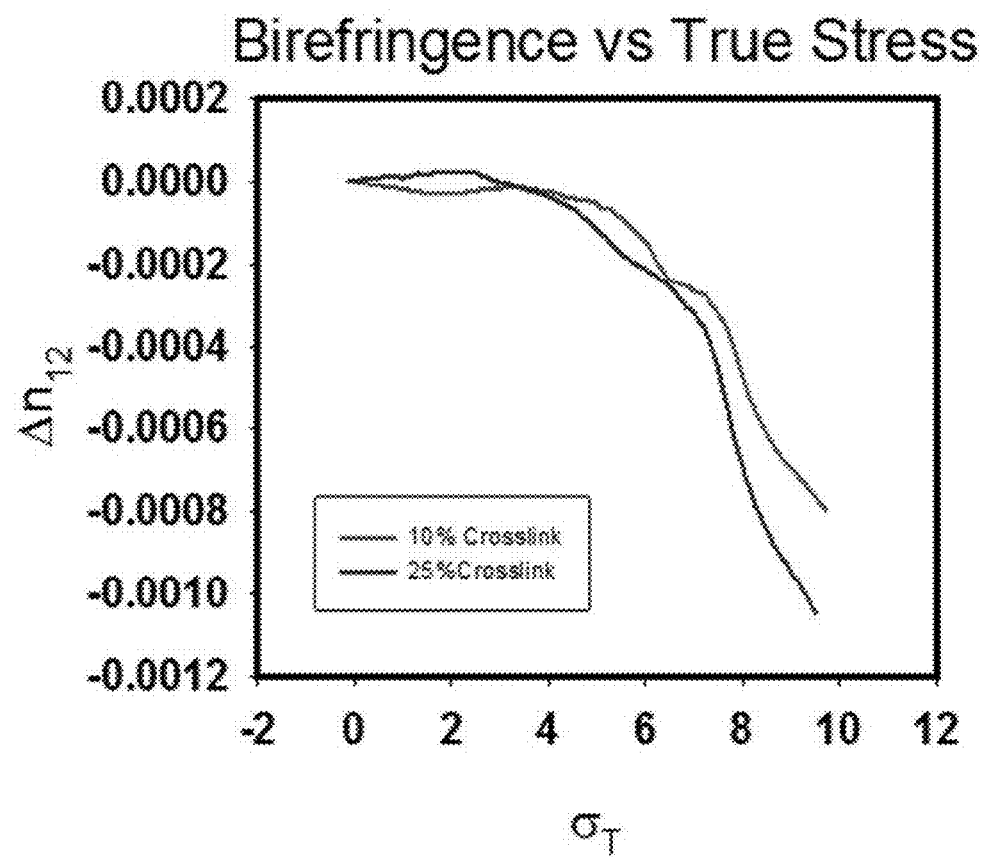
FIG. 9B is a graph showing mechanicano-optical property comparisons between 2% PDMS APCN membranes with different crosslinking ratios.
Figure 10A:
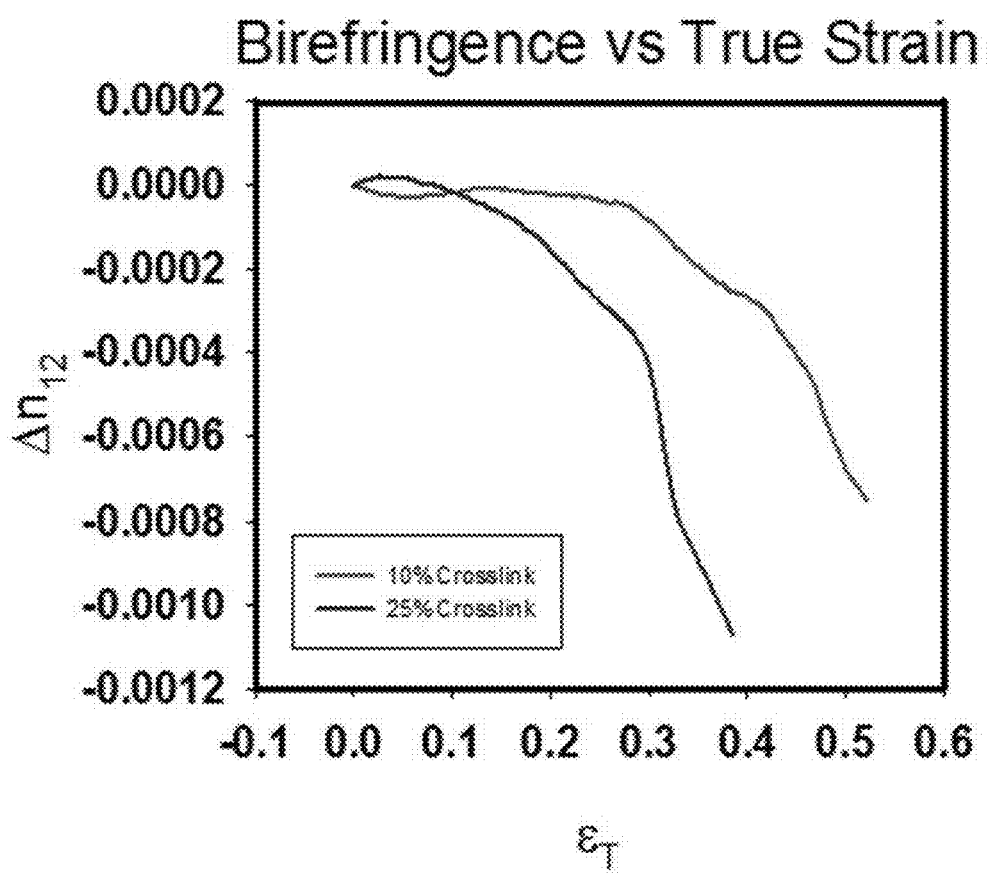
FIG. 10A is a graph showing mechano-optical property comparisons between 5% PDMS APCN membranes with different crosslinking ratios.
Figure 10B:
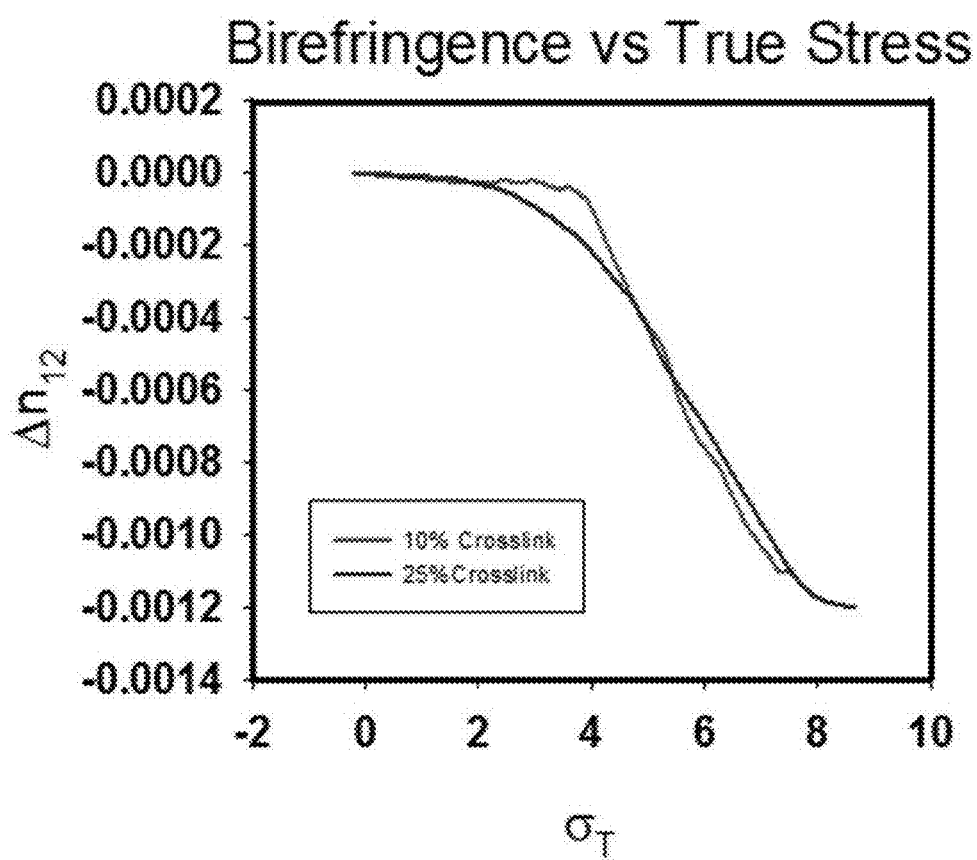
FIG. 10B is a graph showing mechano-optical property comparisons between 5% PDMS APCN membranes with different crosslinking ratios.
Figure 11:
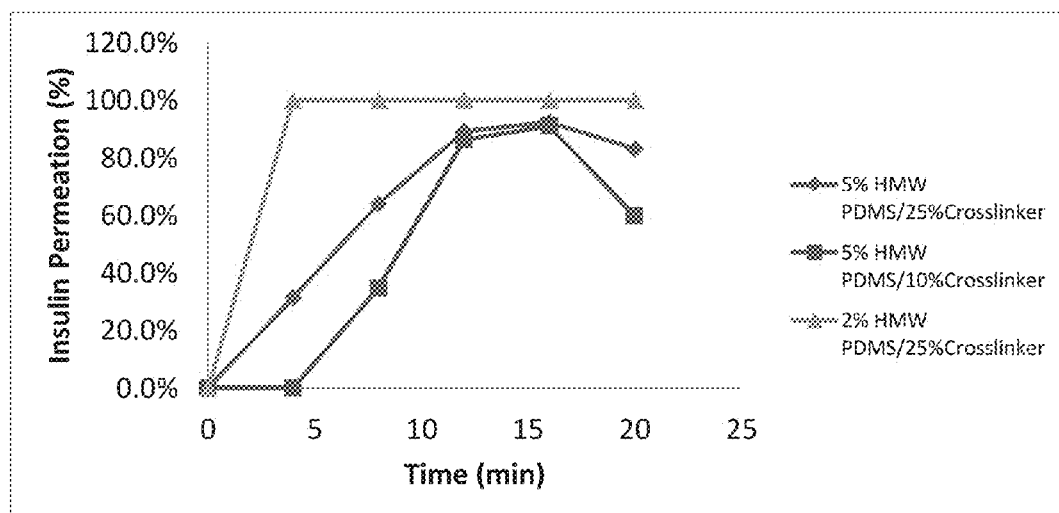
FIG. 11 is a graph showing short time tests on insulin permeation of membranes with a variety of APCN composition and crosslinkinkage.
Figure 12:
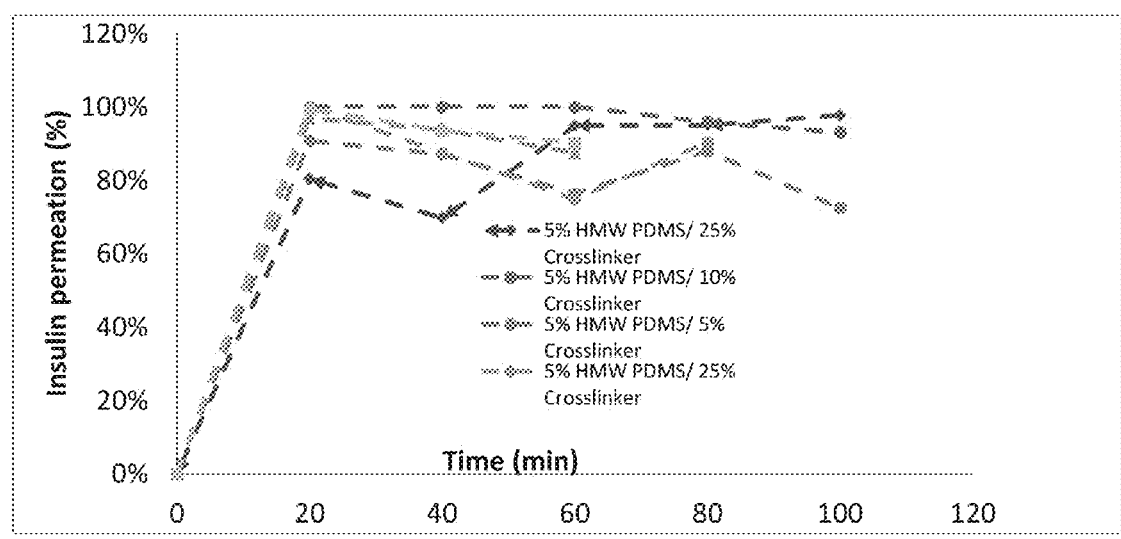
FIG. 12 is a graph showing long time tests on IgG permeation of membranes with a variety of APCN composition and crosslinkinkage.
Figure 13:
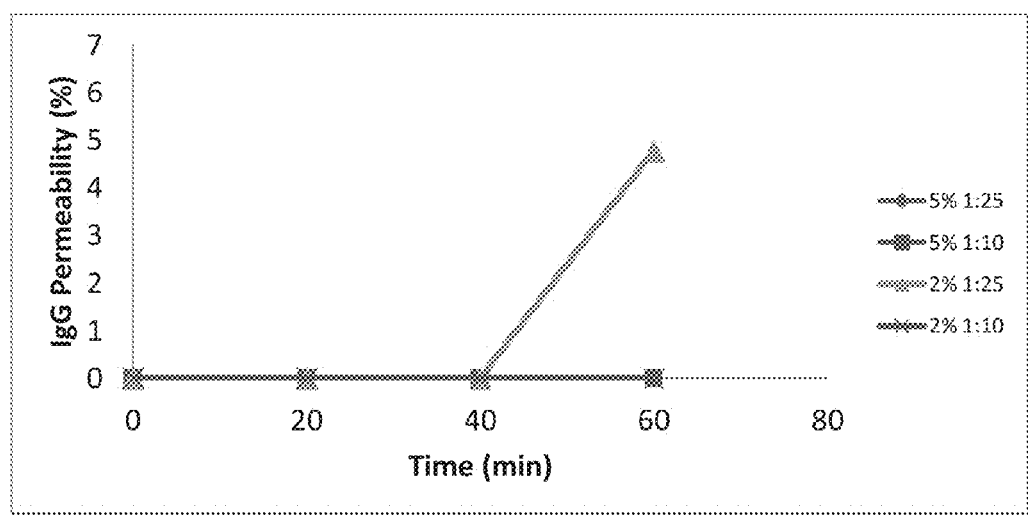
FIG. 13 is a graph showing short time tests on IgG permeation of membranes with a variety of PDMS APCN composition and crosslinkink levels.
Figure 14:
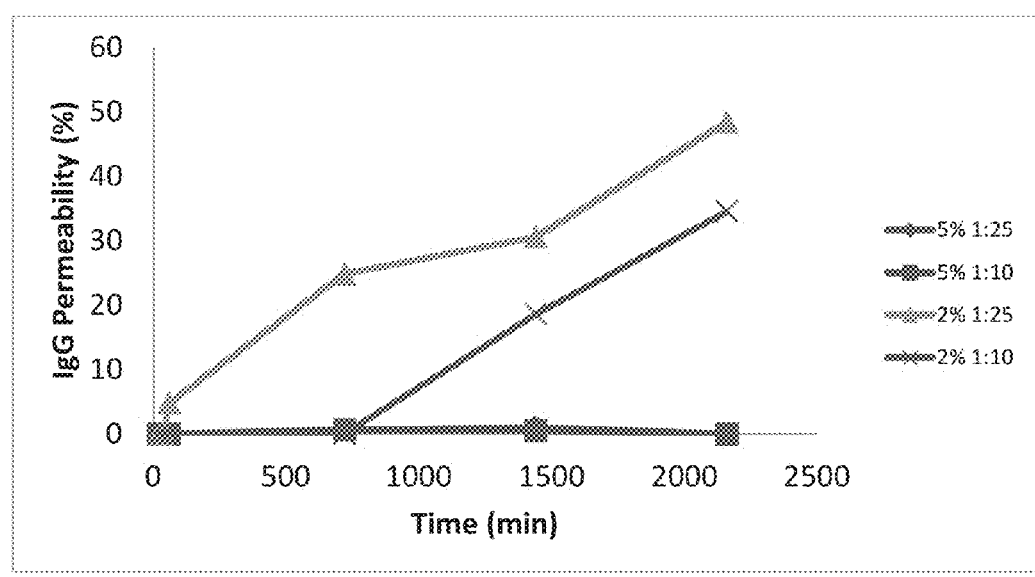
FIG. 14 is a graph showing long time tests on IgG permeation of membranes with a variety of PDMS APCN composition and crosslinkink levels.
Figure 15A:
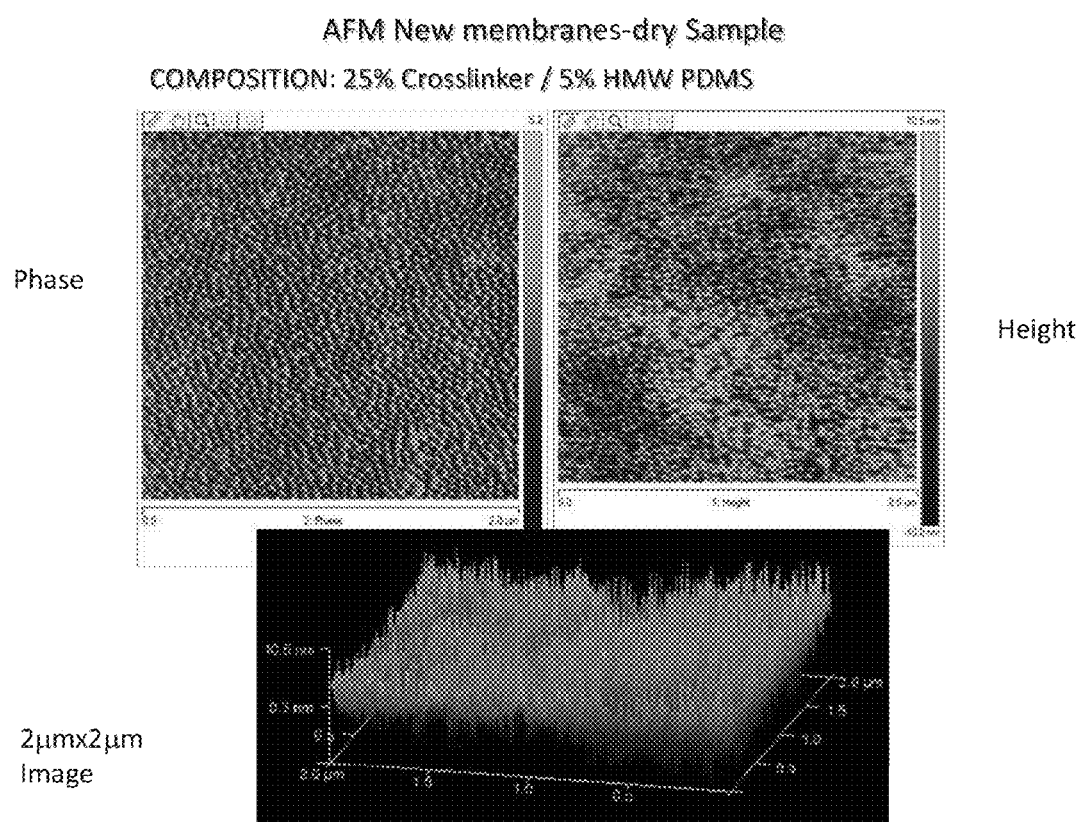
FIG. 15A is a graphic providing AFM phase and height images for 5% PDMS APCN with 1:25 crosslinking with 2 μm scale.
Figure 15B:
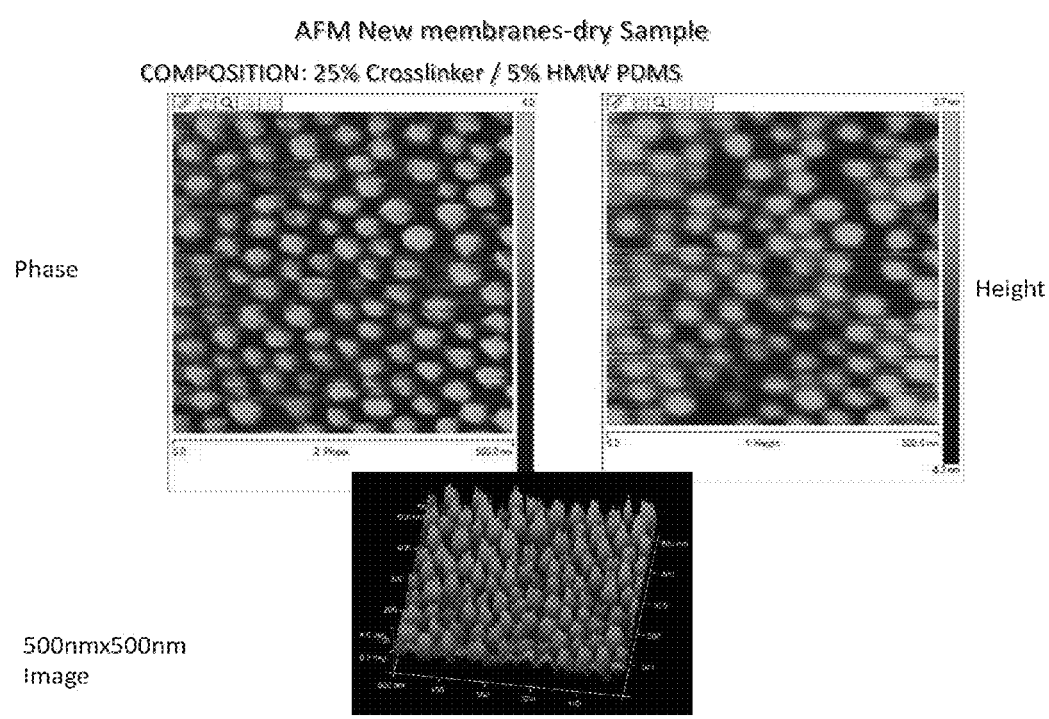
FIG. 15B is a graphic providing AFM phase and height images for 5% PDMS APCN with 1:25 crosslinking with 500 nm scale.

Mechanical-optical Test Results:

FIG. 9 shows strain optical and stress optical behavior of 10-25% crosslink at 2% PDMS APCN. The data indicate that these polymers exhibit negative intrinsic birefringence and chain orientation (molecular level strain) almost linearly correlated with the macroscopic strain that is applied. Stress optical behavior is found to be quite non-linear.

At 5% APCN both crosslinking levels indicate the strain optical and stress optical behaviors are nonlinear though the polymer is still exhibit negative intrinsic birefringence ($\Delta N_{12} = n_1 - n_2$) 1=stretching direction, 2=transverse direction)birefringnece become increasingly negative as the films are stretched Permeabilities The permeability tests were conducted using a pre-described diffusion chamber. ~60-160 μm thick membranes having a diffusion area of 2 cm$^2$ were placed between the receiver and donor chambers and mixed at 37° C. The systems were mixed at 150 rpm to eliminate the boundary layer effect in a G24 Environmental incubator shaker from New Brunswick Scientific.

Permeability P can be obtained from the slope of $-\ln(\Delta Ct/\Delta C0)$ versus time plots, and using $$\frac{(C_{d,t} - C_{r,t})}{(C_{d,0} - C_{r,t})} = \frac{\Delta C_t}{\Delta C_0} = \exp(-P\beta t)$$

Where Cd,0 and Cd,t are concentrations of a solute in the donor chamber at time t=0 and t, and Cr,0 and Cr,t are those in the receiving chamber at t=0 and time t, respectively. The diffusion cell constant ($\beta$) can be calculated by:

$$\beta = \frac{A}{L}(V_d^{-1} + V_r^{-1})$$

Insulin Permeability

Insulin permeability tests were carried out using 400 μg/ml insulin (bovine, containing ~0.5% zinc,) concentration in PBS in the donor chamber. To prevent the formation of insulin aggregates, solutions were stabilized with 0.15% n-octyl β-D-glucopyranoside and 0.05% sodium azide was added as anti-bacterial. The sets of experiments were separated into two groups of short and long time experiments to be able to get sufficient amount of material out of the 2 ml receiver chamber for enzyme-linked immunoabsorbent assays. For the short time experiments, a 100 μl of sample was taken every 5 min for the first 20 min and for the long time experiment same amount is taken every 20 min for 100 min. Insulin concentrations were determined using an insulin enzyme-linked immunoabsorbent assay (ELISA) kit from microplate colors using a spectrophotometer at the North East Ohio Medical School (NEOMED) Spectramax Plus operated at 505 nm.

The diffusion of Insulin is faster than in the previous generation with a 100% permeation in less than 20 min.

IgG Permeability

IgG permeability tests were carried out using 800 μg/ml human IgG concentration in the donor chamber. The sets of experiments were separated in the same way with insulin permeability experiments. For the short time experiments, 100 μl of sample was taken every 20 min for the first 60 min and for the long time experiment same amount is taken every 12 hours for 1.5 days. Insulin concentrations were determined using a human IgG enzyme-linked immunoabsorbent assay (ELISA) kit from microplate colors using a spectrophotometer in NEOMED Spectramax Plus operated at 450 nm.

The ability of the membranes to stop/delay the diffusion of IgG has a strong relationship with the amount of HMW PDMS. The samples with the highest concentration of HMW PDMS (5%) had the best IgG blockage.

Morphology

AFM

Solution cast and cured samples were used in AFM experiments. The height and phase images were obtained by using a Nanoscope III Multimode microscope from Digital Instruments operating in the tapping mode with aluminum-coated AFM probe (Nanosensors_ PPP-NCHR, length 125 mm, width 30 mm, thickness 4 mm, 330 kHz frequency).

The polymer with a higher concentration of both the HMW PDMS and crosslinker exhibited the highly ordered, homogeneous channel like morphology acting as perfect chromatographic column for insulin and IgG separation.

Device Preparation

Figure 16:
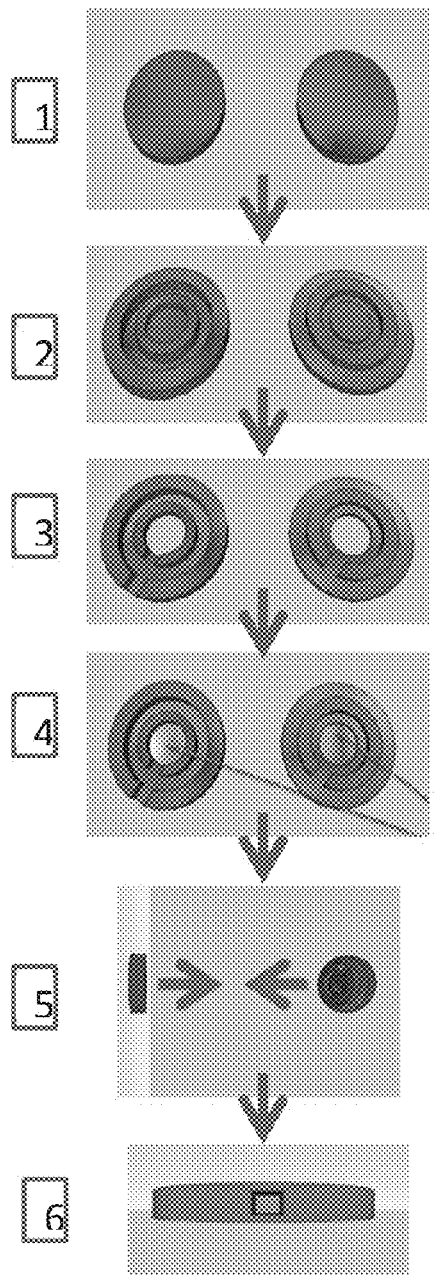
FIG. 16 provides a scheme for device preparation.
Figure 17A:
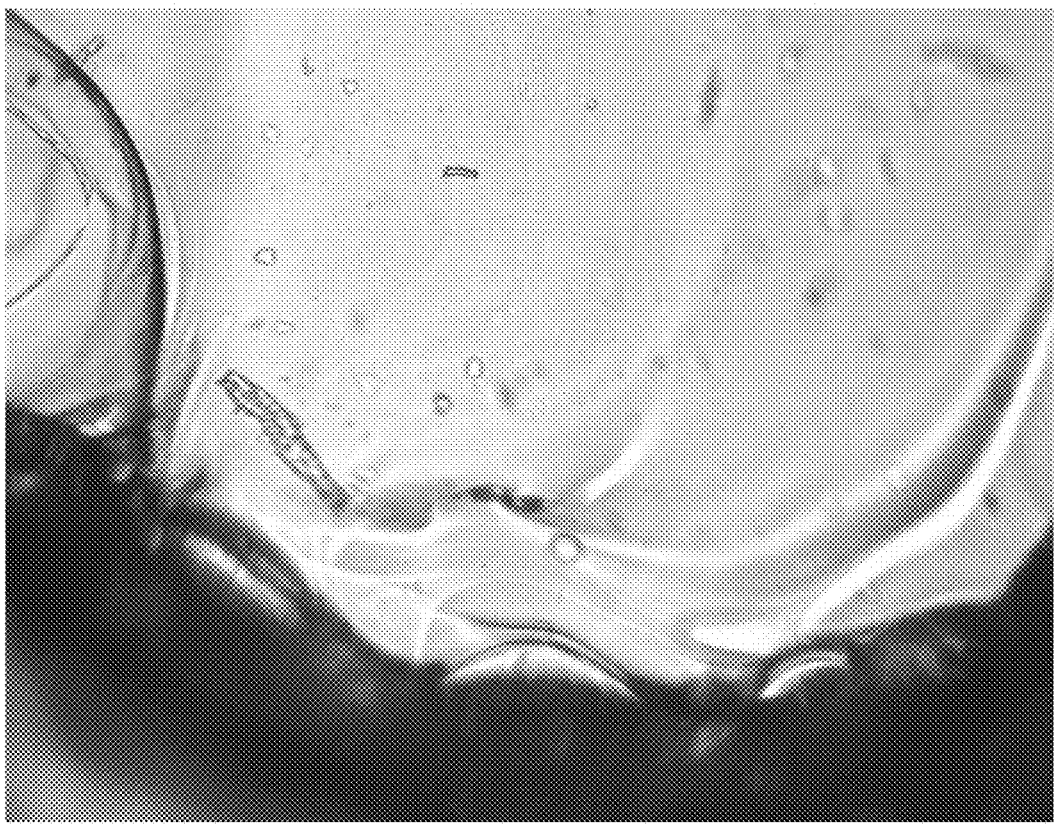
FIG. 17A is a microscopy images of BAP device membrane after 3 weeks in buffer saline solution.
Figure 17B:
FIG. 17B is a microscopy images of BAP device membrane after 3 weeks in buffer saline solution.

Our BAP consists of the APCN membrane deposited on a flexible but stiff scaffold. The preparation of the device until Islets of Langerhans addition and complete seal with a biocompatible silicone elastomer can be seen from FIG. 16.

Optical Microscopy

The BAP device was immersed in a petri dish filled with buffer saline solution for 3 weeks to evaluate the interface connectivity of scaffold and membrane as well as the overall device integrity.

There is no tear or holes on the membrane even after 3 weeks in buffer solution. Some wrinkles can be observed due to the swelling property of the membrane which did not changed the device integrity.

Enhancement of Membrane Strength in Swollen State:

In order to enhance the strength of the membrane, nanofiber reinforcement process may be implemented. This is typically accomplished as follows.

Following the scaffold manufacturing and punching out the hole in the center of both walls, electrospinning of a suitable dope (fiber precurser) is affected. For this a variety of materials could be used. These include biocompatible polyurethanes, rubbers, etc that have physical and/or chemical affinity to membrane material for interfacial strength.

One preferred method is to develop electrospinnable formulation that in turn including the same family of material developed in this patent disclosure. By increasing the high molecular weight PDMS concentration and increasing the solution viscosity (through reduction of solvent content) one could obtain electrospinnably solution (dope). This in-turn, is used to create a thin nanomat (web) of nanofibers criss-crossing the opening of the device. When needed curing step is added facilitating increased strength within the nanofibers and at the junctions where they touch each other facilitating stronger interfiber bonding. Following this process the membrane precursor is delivered to this nanomat taking care that the nanofibers are uniformly coated. Subsequent curing and closure of the two halves of the device and opening of the islet delivery hole completes the process of making the devices.

Various modifications and alterations that do not depart from the scope and spirit of this invention will become apparent to those skilled in the art. This invention is not to be duly limited to the illustrative embodiments set forth herein.

What is claimed is:

1. A method of preparing an amiphiphilic co-network comprising
preparing a molecularly-bimodal crosslinkable amphiphilic graft by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture where the molar mass ratio between average molar mass of the first asymmetric-telechelic monomer mixture polydihydrocarbylsiloxane and average molar mass of the second asymmetric-telechelic monomer mixture polydihydrocarbylsiloxane is between 1:2 and 1:20; and
crosslinking the molecularly-bimodal crosslinkable amphiphilic graft with a siloxane compound that includes at least two Si—H bonds.

2. The method of claim 1, where the second asymmetric-telechelic polydihydrocarbylsiloxane monomer mixture is 0.1% to 10% of the total asymmetric-telechelic polydihydrocarbylsiloxane monomer.

3. The method of claim 1, where the first asymmetric-telechelic polydihydrocarbylsiloxane monomer mixture includes:

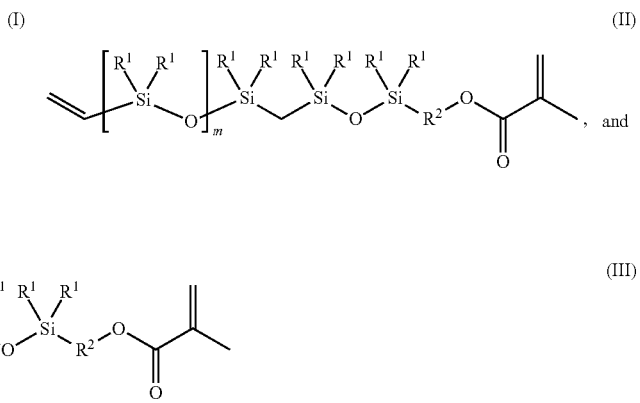

where each $R^1$ is individually a monovalent organic group, each $R^2$ is individually a divalent organic group, and each m is individually an integer from about 190 to about 320 units.

4. The method of claim 3, where the first asymmetric-telechelic polydihydrocarbylsiloxane monomer mixture is prepared by reacting a vinyl telechelic polydihydrocarbylsiloxane with a disiloxane acrylate with a telechelic polydihydrocarbylsiloxane to disiloxane acrylate molar ratio of less than 1:2; where the vinyl telechelic polydihydrocarbylsiloxane is defined by the formula

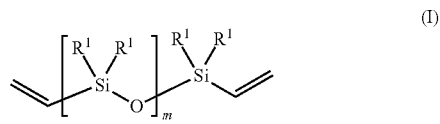

where each $R^1$ is individually a monovalent organic group, and wherein the disiloxane acrylate defined by the formula

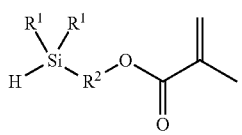

(IV)

where each R¹ is individually a monovalent organic group, and R² is a divalent organic group.

5. The method of claim 3, where each R¹ is an alkyl group of 1 to 6 carbon atoms.

6. The method of claim 1, where the second asymmetric-telechelic polydihydrocarbylsiloxane monomer mixture includes the following:

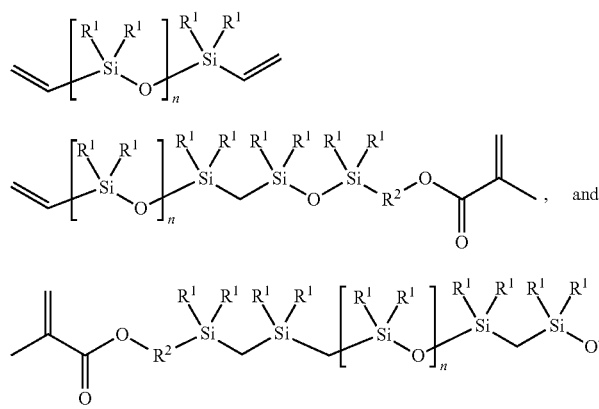

(V)

(VI)

(VII)

where each R¹ is individually a monovalent organic group, each R² is individually a divalent organic group, and each n is individually an integer from about 1100 to about 1900.

7. The method of claim 6, where the second asymmetric-telechelic polydihydrocarbylsiloxane monomer mixture is prepared by reacting a vinyl telechelic polydihydrocarbylsiloxane with a disiloxane acrylate with a telechelic polydihydrocarbylsiloxane to disiloxane acrylate molar ratio of less than 1:2; where the vinyl telechelic polydihydrocarbylsiloxane is defined by the formula

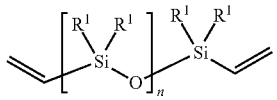

(VIII)

where each R¹ is individually a monovalent organic group, and each n is individually an integer from about 1100 to about 1900; and wherein the disiloxane acrylate defined by the formula

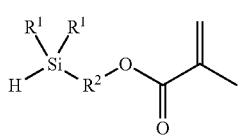

(IV)

where each R¹ is individually a monovalent organic group, and R² is a divalent organic group.

8. The method of claim 6, where each R¹ is an alkyl group of 1 to 6 carbon atoms.

9. The method of claim 1, where the dihydrocarbylacrylamide monomer is defined by the formula

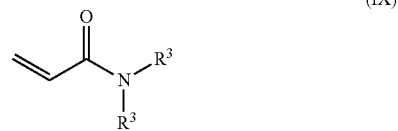

(IX)

where each R³ is individually a monovalent organic group.

10. The method of claim 9, where the dihydrocarbylacrylamide monomer is defined by the formula

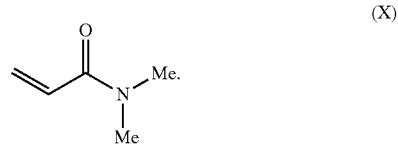

(X)

11. The method of claim 1, where the dihydrocarbylacrylamide monomer is between 40 and 60 wt % of the total weight of the dihydrocarbylacrylamide monomer, first asymmetric-telechelic polydihydrocarbylsiloxane monomer mixture, and second asymmetric-telechelic polydihydrocarbylsiloxane monomer mixture.

12. The method of claim 1, where the step of crosslinking the molecularly-bimodal crosslinkable amphiphilic graft with a siloxane compound that includes at least two Si—H bonds includes the use of a Karstedt catalyst to facilitate crosslinking.

13. The method of claim 1, where the siloxane compound that includes at least two Si—H bonds is defined by the formula

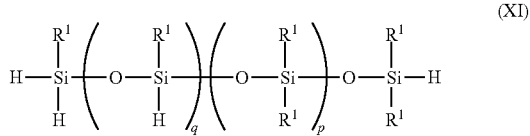

(XI)

where each $R^1$ is individually a monovalent organic group, q is an integer from about 1 to about 2000 and p is an integer from about 1 to about 2000.

14. The method of claim 13, where each $R^1$ is an alkyl group of 1 to 6 carbon atoms.

15. An amiphiphilic co-network prepared by the method of claim 1.

16. A bio-artificial organ comprising
a housing with a plurality of holes on the housing, over the plurality of holes, an amiphiphilic co-network prepared by
preparing molecularly-bimodal crosslinkable amphiphilic graft by polymerizing a dihydrocarbylacrylamide monomer in the presence of a first asymmetric-telechelic polydihydrocarbylsiloxane monomer mixture and a second asymmetric-telechelic polydihydrocarbylsiloxane monomer mixture where the molar mass ratio between average molar mass of the first asymmetric-telechelic monomer mixture polydihydrocarbylsiloxane and average molar mass of the second asymmetric-telechelic monomer mixture polydihydrocarbylsiloxane is between 1:2 and 1:20; and crosslinking the molecularly-bimodal crosslinkable amphiphilic graft with a siloxane compound that includes at least two Si—H bonds.

17. The bioartifical organ of claim 16, where the housing comprises
a first disc with a with a first raised ring around the perimeter of the disc and a concentric smaller second raised ring within the first raised ring, and
a second disc with a raised ring, the raised ring of the second disc situated between the first and second raised rings of the first disc,
wherein a void is present between the first disc, the second raised ring of the first disc, and the second disc, and the first disc, the second disc or both discs include a plurality of holes that connect to said void.

18. The bioartifical organ of claim 17, where the first raised ring and second raised ring of the first disc includes a cut out portion, and
the raised ring of the second disc includes a cutout portion aligned with the cut out portion of the first disc.

* * * * *